US006174680B1

(12) United States Patent
Makrigiorgos

(10) Patent No.: US 6,174,680 B1
(45) Date of Patent: Jan. 16, 2001

(54) METHOD FOR IDENTIFYING MISMATCH REPAIR GLYCOSYLASE REACTIVE SITES, COMPOUNDS AND USES THEREOF

(75) Inventor: Gerassimos M. Makrigiorgos, Jamaica Plain, MA (US)

(73) Assignee: Dana-Farber Cancer Institute, Inc., Boston, MA (US)

(*) Notice: Under 35 U.S.C. 154(b), the term of this patent shall be extended for 0 days.

(21) Appl. No.: 09/224,227

(22) Filed: Dec. 30, 1998

Related U.S. Application Data

(60) Provisional application No. 60/075,542, filed on Feb. 23, 1998, now abandoned.

(51) Int. Cl.[7] .............................. C12Q 1/68; C07H 19/00; C07H 21/00; C07H 21/02; C07H 21/04
(52) U.S. Cl. ........................ 435/6; 435/91.1; 435/91.2; 436/22.1; 436/23.1; 436/24.3; 436/24.31; 436/24.32; 436/24.33; 436/25.32
(58) Field of Search ..................... 435/6, 91.1, 91.2; 536/22.1, 23.1, 24.3, 24.31, 24.32, 24.33, 25.32

(56) References Cited

U.S. PATENT DOCUMENTS

| | | | |
|---|---|---|---|
| 5,418,149 | 5/1995 | Gelfand et al. .......... | 435/91.2 |
| 5,459,039 | 10/1995 | Modrich et al. .......... | 435/6 |
| 5,516,663 | 5/1996 | Backmann et al. ........ | 435/91.2 |
| 5,780,233 | * 7/1998 | Guo et al. ................ | 435/6 |

OTHER PUBLICATIONS

Zimmermann et al. "DNA streching on functionalized gold surfaces" Nucleic Acids Research, vol. 22, 1994.*
Nakamura et al. "Highly sensitive apurinic/apyrimidinic site assay can detect spontaneous and chemically induced depurination under physiological conditions" Cancer Research, vol. 58, pp. 222–225, Jan. 1998.*
M. Talpaert–Borle et al., *Biochimica Biophysica Acta.*, 740:410–416 (1983).
L. Wodicka et al., *Nature Biotechnology*, 15:1359–1367 (1997).
R. Cotton et al., *GProc Natl. Acad. Sci. USA*, 85:4397–4401 (1988).

* cited by examiner

Primary Examiner—Jezia Riley
(74) Attorney, Agent, or Firm—Nixon Peabody LLP

(57) ABSTRACT

The present application discloses a method of identifying mutations in a target DNA sequence. The method involves:

(a) hybridizing the target DNA sequence with a control DNA sequence wherein said control DNA sequence is the wild-type DNA sequence corresponding to the target DNA sequence to create a duplex;

(b) treating the duplex to remove any spontaneous aldehydes;

(c) reacting the duplex with a repair glycosylase to convert any mismatched sites in the duplex to reactive sites containing an aldehyde-containing abasic site;

(d) reacting the duplex with a compound of the formula X-Z-Y, wherein X is a detectable moiety, Y is $NHNH_2$, $O-NH_2$ or $NH_2$, and Z is a hydrocarbon, alkyhydroxy, alkylethoxy, alkylester, alkylether, alkylamide or alkylamine, wherein Z may be substituted or unsubstituted; and wherein Z may contain a cleavable group; for a sufficient time and under conditions to covalently bind to the reactive sites;

(e) detecting the bound compound to identify sites of mismatches;

(f) determining where the mismatch occurs; and (g) determining whether the mismatch is a mutation or polymorphisms.

30 Claims, 13 Drawing Sheets

A.L.B.U.M.S: ALDEHYDE - LINKER - BASED ULTRASENSITIVE MISMATCH SCANNING.

1. ISOLATE mRNA FROM CANCEROUS AND NORMAL TISSUE. GENERATE cDNA LIBRARY FOR GENES TO BE SCREENED.

2. 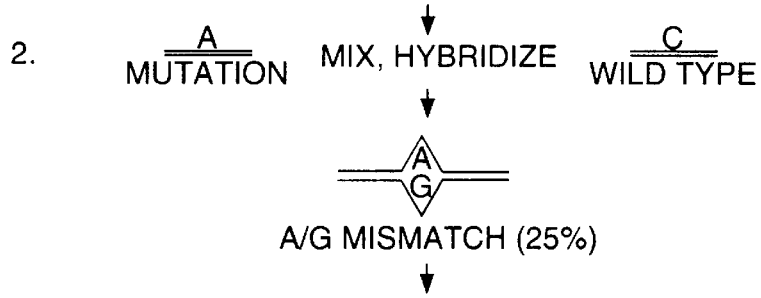

A/G MISMATCH (25%)

3. TREAT w. MISMATCH REPAIR GLYCOSYLASES.
   LABEL RESULTING ALDEHYDES w. FARP.
   IMMOBILIZE FARP - LABELED DNA ON MICROPLATES.

4. DETECT TOTAL MUTATION VIA CHEMILUMINESCENCE.
   ISOLATE AND RECOVER MUTATED DNA, PCR.
   IDENTIFY MUTATION - CONTAINING GENES
   ON DNA ARRAYS FOR HUNDREDS/THOUSANDS OF GENES.
   ↳ VERIFY BY SEQUENCING

ESTABLISH SINGLE-STEP SCREENING OF HUNDREDS OR THOUSANDS OF GENES IN CANCER SAMPLES FOR MUTATIONS. STREAMLINE AND DISSEMINATE THE TECHNOLOGY.

FIG. 1
TECHNOLOGY FOR ISOLATING AND IDENTIFYING MUTATIONS OVER HUNDREDS OR THOUSANDS OF GENES SIMULTANEOUSLY: AN EXAMPLE OF SCREENING FOR A-TO-C TRANSVERSIONS.

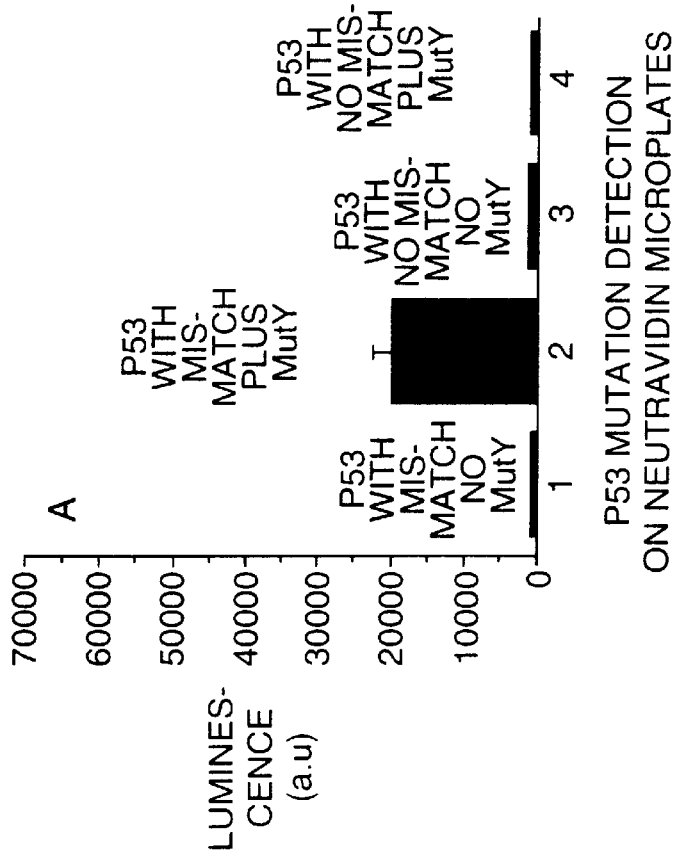

M13 mp19 DNA TESTED.
A = DNA ALONE
B = DNA PLUS MUTY
C = DNA PLUS 5mM METHOXYAMINE PLUS MUTY
D = DNA PLUS 5mM AED PLUS MUTY
E = DNA PLUS 10mM AED PLUS MUTY
F = DNA PLUS 5mM BARP PLUS MUTY

METHOD FOR IDENTIFYING MISMATCH REPAIR GLYCOSYLASE REACTIVE SITES, COMPOUNDS AND USES THEREOF

The present application claims benefit under 35 USC §119 (e) of U.S. Provisional Application Serial No. 60/075,542 filed Feb. 23, 1998, now abandoned.

STATEMENT AS TO FEDERALLY SPONSORED RESEARCH

This invention was made with Government support under grants R29 CA63334, K04 CA69296, and RO1 CA72046, awarded by the USPHS. The Government may have certain rights in the invention.

FIELD OF THE INVENTION

The present invention is directed to methods for identifying and labeling glycosylase-recognizable sites on nucleic acids, and to novel compounds that bind to such glycosylase-recognizable sites on nucleic acids. In a preferred embodiment the method can be used to identify mutations and/or polymorphisms on a nucleic acid segment, or in an arbitrary mixture of nucleic acid segments or genes.

BACKGROUND OF THE INVENTION

The detection of mutations has been an area of great interest in recent years. For example, mutations in certain genes have been associated with a variety of disorders—ranging from blood disorders to cancers. Genetic tests are thus becoming an increasingly important facet of medical care. Consequently, there has been an emphasis on the ability to rapidly and efficiently detect mutations and polymorphisms.

Many electrophoretic techniques have been developed to rapidly screen DNAs for sequence differences by which such mutations can be detected. Denaturing Gradient Get Electrophoresis (DGGE) [Myers, R. M., Maniatis, T. and Lerman, L., *Methods in Enzymology*, 155, 501–527 (1987)], Constant Denaturant Gel Electrophoresis (CDGE) [Borresen, A. L., et al., Proc. Nat. Acad. Sci. USA, 88, 8405 (1991)], Single Strand Conformation Polymorphism (SSCP) [Orrita, M., et al., *Proc. Nat. Acad. Sci. USA*, 86, 2766–2770 (1989)], Heteroduplex Analysis (HA) [Nagamine, C. M., et al., *Am. J. Hum, Genet.*, 45,377–399 (19?9)] and Protein Truncation Test (PTT) [Roest, P. A. M., et al., Hum. Molec. Genet., 2,1719–1721 (1993)] are frequently used methods. Many labs use combinations of these methods to maximize mutation detection efficiency. All these methods require gel electrophoresis. Methods that do not require gel electrophoresis also exist. For example, selective hybridization on immobilized target sequences allows screening for rare known mutations [Zafiropoulos, A., et al., *Biotechniques* 223, 1104–1109 (1997)], while mass-spectrometry has been used to detect mutations by analyzing molecular weight of proteins [Lewis, J. K., et al., *Biotechniques* 24, 102–110 (1998)].

A fundamental problem with currently existing mutation and polymorphism detection methods is that they only screen for mutations on a single gene at a time (i.e. the method is directed to looking at a 'gene of interest', that is suspected of having a mutation). Given that the human genome has 50,000–100,000 genes, this is a severe limitation. It is likely that unknown mutations and polymorphisms in several other genes both known and unknown, exist simultaneously with mutations/polymorphisms in the 'gene of interest'. However, mutations in those other genes would likely not be identified. Therefore a method that can perform 'mutation/polymorphism scanning' in for a wide array of genes simultaneously, without the initial need for identifying the gene one is screening would be useful. Gel-electrophoresis-based methods are essentially restricted to examining mutations in a single gene at a time. Attempts have been made to devise non-gel electrophoretic methods to identify mutations, that would not be restricted to a single gene [Cotton et al., *Proc. Natl. Acad. Sci. USA* vol. 85, pp 4397–4401, (1988)] [Nelson, S. F. et al., *Nature Genetics*, 4, 11–8, (May 1993)] [Modrich, P., et al., Methods for Mapping Genetic Mutations. U.S. Pat. No. 5,459,039, (1995)]. These methods, however, have had limited success [Nollau P and Wagener C., *Clinical Chemistry* 43: 1114–1128 (1997)] since they are complicated, typically requiring several enzymatic steps and they result in a large number of false positives, i.e. they frequently score mutations and polymorphisms in normal DNA. It would be desirable to have a method that allows highly sensitive and specific identification and rapid purification of sites that contain mutation/polymorphism over large spans of the genome.

Although DNA arrays and methodologies that can simultaneously scan a large set of DNA fragments for gene expression (e.g. the 'repertoire' and amount of genes expressed in normal vs. cancer cells) are known [Wodicka L, *Nature Biotechnology* 15: 1359–1367 (1997); Lockhart, D J, *Nature Biotechnology* 14: 1675–1680 (1996); Schena, M., *Trends Biotecnnol* 16: 301–306, (1998); Yang, T. T., *Biotechniques* 18: 498–503, (1995)], the ability to scan a large set of random DNA fragments for unknown mutations is a much more demanding process on which the technology is lagging [Ginot F., *Human Mutation* 10: 1–10 (1997)]. Thus far DNA array-based methods to scan for polymorphisms (SNPs) and mutations has been restricted to specific genes [Lipshutz, R. J., *Biotechniques* 19: 442–447 (1995); Wang, D. G., *Science* 280: 1077–1082 (1998)]. Whereas detection of unknown mutations over several genes requires a selectivity and sensitivity not currently achievable by present arrays [Ginot F., *Human Mutation* 10: 1–10 (1997)]. For example, when it comes to unknown mutation detection, even a single gene with a coding sequence of the size of APC (8.5 kb) is difficult to screen in a single experiment, especially when an excess normal alleles is simultaneously present [Sidransky D., *Science* 278: 1054–1058 (1997)]. A method that permits identification of mismatches over large spans of the genome would be desirable.

The process of mismatch repair of nucleic acids has also received considerable attention in recent years with the elucidation of systems in microorganisms such as *E. coli,* and more recently, mammals including humans. For example, continuous cellular damages occur to nucleic acids during the cell life cycle; for example damage resulting from exposure to radiation, or to alkylating and oxidative agents, spontaneous hydrolysis and errors during replication. Such damages must be repaired prior to cell division. There are a number of different cellular repair systems and a variety of components that participate in these systems. One component is represented by the class of DNA repair enzymes known as mismatch repair glycosylases. These enzymes convert mismatches in DNA to aldehyde-containing abasic sites. These abasic sites can also occur by other means. For example, they can occur spontaneously, or following deamination of cytosine to uracil and subsequent removal of uracil by uracil glycosylase [Lindahl and Myberg, 1972; Lindahl, 1982 & 1994; Demple and Harrison, 1994; von Sonntag 1987; Loeb and Preston, 1986]. It has been estimated that almost 10,000 abasic sites are generated per cell per day [Lindahl and Nyberg, 1972]. Finally abasic sites are generated by DNA damaging agents such as ionizing radiation [von Sonntag, 1987], reactive oxygen intermediates [Ljungman and Hanawalt, 1992; Lindahl, 1994], antibiotics [bleomycin-iron complexes, neocarzinostatin, Povirk and Houlgrave, 1988], or alkylation agents [methylmethanesulfonate, dimethylsulfate etc., Loeb and Preston—1986]. Unrepaired abasic sites can be lethal or promutagenic lesions since during DNA replication DNA polymerases insert primarily adenines opposite them [Kunkel et al.—1983; Loeb and Preston—1986]. Closely-spaced abasic sites generated within a few base pairs of each other by damaging agents may be a particularly significant set of lesions, as they may hinder repair [Chaudhry and Weinfeld, 1995a, 1997; Harrison et al., 1998], or they can be enzymatically converted to double strand breaks or other complex multiply-damaged sites [Dianov et al., 1991]. It has been postulated that such complex forms of DNA damage may be particularly difficult for cells to overcome [Ward 1985, 1988; Wallace, 1988; Goodhead, 1994; Chaudhry and Weinfeld, 1995a and b, and 1997; Rydberg, 1996; Hodgkins et al., 1996; Nikjoo et al., 1998; Harrison et al., 1998]. Quantification of the overall number of abasic sites directed to looking at abasic sites resulting from DNA damage has been reported [Futcher and Morgan, 1979; Talpaert-Borle and Liuzzi, 1983; Weinfeld and Soderlind, 1991; Ide et al., 1993; Chen et al., 1992; Kubo et al., 1992]. The binding efficiency of such systems has been relatively low.

SUMMARY OF INVENTION

We have now discovered a method that permits the rapid identification of mutations in a DNA segment or in any mixture of DNA segments (genes). This method comprises identifying mismatches that occur when a target nucleic acid strand is hybridized to a control nucleic acid sequence. The method comprises (a) isolating the nucleic acid, e.g., DNA, to be screened for mutations (referred to as the target DNA), adding PCR primers, and hybridizing it with control DNA, to create mismatches. These mismatches occur at the exact positions of mutations or polymorphisms; (b) removing any pre-existing, spontaneous aldehydes by, for example, treating the DNA with hydroxylamine; (c) using mismatch repair glycosylase enzymes (MutY and TDG) to convert the mismatches to reactive sites, namely, aldehyde-containing abasic sites (these enzymes recognize mismatches and will 'cut' the nucleic acid base, e.g., adenine at that site to create a reactive site); (d) using compounds (e.g. ligands) with functional groups that at one site can covalently bind to the reactive sites on the DNA, and that at a second site contain unique moieties that can be detected; (e) binding antibodies or avidin to the detectable second sites of the DNA-bound ligands. These antibodies or avidin may carry chemiluminescent or other indicators, so that the total reactive sites on the nucleic acid, e.g., DNA segment(s) tested is quantified, e.g. by chemiluminescence; (f) purifying the segments where a reactive site is present (e.g. by immunoprecipitation, or by ELISA-microplate-based techniques, or by microsphere-based techniques). The rest of the nucleic acid, e.g., DNA that does not contain mismatches can then be discarded; (g) amplifying the remaining, mismatch containing nucleic acid, e.g., DNA, by PCR using the primers added in the first step; and (h) analyzing that purified nucleic acid, e.g., DNA by standard gene-detection methods (e.g., hybridization), in order to find which gene each identified mismatch belongs to. Thereafter, by known techniques determining whether that mismatch is a mutation that either causes the disorder or is associated with the disorder or simply an allelic variation, i.e. a polymorphism.

More specifically, the present invention permits biochemical approaches for chemically modifying mutations in a target nucleic acid sequence. The mutations are converted to mismatches following hybridization with control nucleic acid sequence. The mismatches in the hybrid nucleic acid, e.g. DNA can then be converted to aldehydes by mismatch repair enzymes, covalently bound by a ligand molecule, and then identified by a detectable moiety. Subsequently the mismatch-containing DNA can be purified by known means such as immunoprecipitation and the mutation-containing genes detected.

The target nucleic acid can be cDNA or genomic DNA. For example, the DNA can be any mixture containing one or various sizes of DNA, such as cDNA synthesized from the whole mRNA collected from cells that need to be screened for mutation/polymorphism; or fractions thereof; or the whole genomic DNA collected from cells that need to be screened for mutation/polymorphism; or fractions thereof; or any combination of the above digested into smaller pieces by enzymes. The use of cDNA is preferable.

The control will be a wild-type DNA fraction similar to the target nucleic acid. This wild-type DNA likely will have no mutations. In some instances the control DNA will be from a corresponding cell from the same individual not displaying the abnormality being screened for. In many cases the control DNA will be from a corresponding cell from a different individual than the target nucleic acid is from. And in other cases differences within the two alleles in a single cell type will be screened, one allele acting as a control and the second allele acting as target DNA.

The target nucleic acid such as DNA is mixed and hybridized with wild-type DNA to create mismatches at the positions of differences, which are expected to be mutations/polymorphisms. Generic PCR primers are added to the nucleic acids, in order to amplify the preparation at a later stage. The mismatches are then recognized and converted to aldehyde-containing reactive sites by enzymes such as a glycosylase mismatch repair enzyme such as the E. coli MutY, or the thymine DNA glycosylase (TDG) from HeLa cells or from E. coli. A unique feature of these enzymes is that they are highly specific, i.e. they act only on mismatches while they leave non-mismatch containing DNA completely intact.

These reactive sites are identified by using a compound containing an aldehyde-binding moiety such as —O—NH2 (-hydroxylamine), or —NHNH2 (-hydrazine) or —NH2 (-amine) and also having a second moiety that reacts with a detectable entity (e.g. fluorescein, biotin, digoxigenin, which respectively react with antifluorescein antibody, avidin, and antidigoxigenin antibody. The antibodies may have chemiluminescence tags on them and thereby are detected). A unique feature of the present approach is that the aldehyde-binding moiety binds covalently to the enzyme-generated reactive sites. Combined with the specificity of the mismatch-repair enzymes, the use of covalently bound ligands to the position of mutations results in a sensitivity and specificity which is unparalleled by other methods for detection of mutations and polymorphisms.

The bi-functional compounds that bind covalently reactive sites have the general formula:

$$X\text{-}Z\text{-}Y,$$

wherein

X is a detectable moiety, preferably X is NH2, SH, NHNH2, a fluorescein derivative, a hydroxycoumarin derivative, a rhodamine derivative, a BODIPY derivative, a digoxigenin derivative or a biotin derivative;

Y is NHNH2, O—NH2 or NH2, preferably Y is O—NH2; and

Z is a hydrocarbon, alkylhydroxyl, alkylethoxy, alkylester, alkylether, alkylamide or alkylamine. The hydrocarbon chain of Z may contain a cleavable group (e.g. an S—S disulfide bond). Z may also be substituted or unsubstituted. The reactive groups, X and Y, are used for covalent binding to the resulting aldehydes of damaged DNA (Y) and detection by a detecting group (X).

We have also found a method that permits one to overcome resolutions and other limitations existing in current DNA chip technology and utilize the existing DNA chip technology for mutations scanning over hundreds or thousands of genes simultaneously. This method comprises first identifying a DNA segment containing a mismatch. Those mismatches can either be caused by a single nucleotide polymorphism (SNP) or by a base substitution mutation. Thereafter, one selects a DNA segment of from about 50–300 nucleotides containing a mismatch. Those DNA segments can be amplified by PCR and then screened on the DNA chip. Accordingly, instead of selecting a single gene at a time and examining whether it contains mutations, the present methodology first scans DNA to identify and isolate mismatch-containing and thereby mutation-containing DNA fragments (genotypic selection), and then determines which genes these DNA fragments belong to, by using available DNA arrays. Thus, the search for mutations is transformed to the easier task of searching for genes on a DNA array to identify on which gene and gene segment the mismatch occurs. Accordingly, DNA arrays currently used for multiplexed gene expression scanning [Wodicka L, *Nature Biotechnology* 15: 1359–1367 (1997); Lockhart, D J, *Nature Biotechnology* 14: 1675–1680 (1996); Schena, M., *Trends Biotecnnol* 16: 301–306, (1998); Yang, T. T., *Biotechniques* 18: 498–503, (1995)] can be used directly or with minor modifications known to the artisan based upon this disclosure to scan for mutation.

A preferred embodiment of the invention has a general formula;

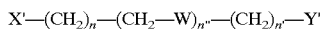

wherein

X' is NHNH2 or NH2, preferably NH2;

Y' is O—NH2 or NH2, preferably O—NH2;

W is —NHC(O)—, —NHC(OH)—, —C(OH)—, —NH—, C—O—, —O—, —S—, —S—S—, —OC(O)—, or C(O)O—;

n is and integer from 0 to 12, preferably 4–7 and more preferably 6;

n' is an integer from 0 to 12, preferably 4–7, and more preferable 6, and n" is an integer from 1 to 4, preferably 1–2, and more preferably 1.

Preferably, the compound has a molecular weight between 100–500, more preferably 100–300, still more preferably 150–200

A preferred compound is 2-(aminoacetylamino) ethylenediamine, or AED (NH$_2$CH$_2$CH$_2$NHC(O)CH$_2$ONH$_2$).

Other compounds are: a fluoresceinated hydroxylamine-containing (—O—NH$_2$) compound (e.g. FARP); a biotinylated hydroxylamine-containing (—O—NH$_2$) compound (BARP, Kubo K, Ide H, Wallace S S, and Kow. Biochemistry 31: 3703–3708, 1992); or hydrazine-containing (—NH—NH2) compounds (e.g. biotin hydrazide; biotin-LC-hydrazide).

When Y=NH$_2$ (amine), in order to remain covalently bound to the aldehyde on DNA, an additional chemical reduction step is required. The conditions for this reduction are well known, e.g. at pH 5–7, in the presence of reducing agent (borohydride).

When X=NH$_2$ (amine), in order for the covalently-bound ligand to be recognizable by an antibody, the free —NH$_2$ group is first covalently linked to an amine-binding compound with a recognizable group (e.g. a succinimidylester compound such as biotin-LC-succinimidyl ester; biotin-LC-SS-succinimidyl ester (Pierce); fluorescein-succinimidyl ester; etc.). The reaction and purification conditions of such succinimidyl esters with —NH$_2$ containing compounds are well known.

When X=SH (sulfhydryl), in order for the covalently-bound ligand to be recognizable by an antibody, the free —SH group is first covalently linked to a sulfhydryl-binding compound with a recognizable group (e.g. a maleimide compound such as biotin-LC-maleimide; biotin-LC-SS-maleimide (Pierce); fluorescein-maleimide; etc.). The reaction and purification conditions of such maleimides with —SH containing compounds are well known.

Once these compounds are covalently bound to the reactive sites, their reaction with a detectable entity such as antibodies (e.g. avidin, antifluorescein etc.) and their subsequent detection (e.g. chemiluminescence) and purification (e.g. immunoprecipitation, or avidin-coated microplates, or avidin-coated microspheres) are well known in the art.

BRIEF DESCRIPTION OF THE FIGURES

FIG. 1 shows a schematic of how the present technology is applied for identification of mutations in a complex mixture of genes, e.g. screening for C to A transversions over hundreds or thousands of genes simultaneously.

FIG. 4A shows detection of AP sites in genomic calf thymus DNA depurinated for 15 seconds, without treatment (bar 1) or following treatment (bar 2) with hyrdoxylamine.

FIG. 4B shows detection of spontaneously generated AP sites in hydroxylamine-treated genomic calf thymus DNA at pH=7.0, at a temperature of 37° C. (curve 1) or 4° C. (curve 2).

FIG. 5A shows 49-mer double stranded oligonucleotides that are MutY-treated and visualized on polyacrylamide gels following SYBR GOLD staining. Lane 1, No mismatch, no MutY. Lane 2, no mismatch, plus MutY. Lane 3, A/G mismatch, no MutY. Lane 4, A/G mismatch, plus MutY.

FIG. 5B shows double standard homoduplex mixtures (DNA ladder, 27–500 base pairs) are MutY-treated and visualized on polyacrylamide gels following SYBR GOLD staining. Lane 1, no MutY. Lane 2, plus MutY.

FIG. 5C shows single stranded M13 DNA (7,249 bases) are enzymatically-treated and visualized on agarose gels following ethidium staining. Lane 1, M13 DNA, no MutY. Lane 2, M13 DNA, plus MutY. Lanes 3–6, molecular weight markers.

FIG. 8A shows chemiluminescence from single stranded M13 DNA (that forms ~3 mismatches over 7249 bases) and double stranded homoduplex M13 DNA (no mismatches) enzymatically-treated by MutY, BARP-labeled and captured on microplates. Bar 1, s.s. M13 DNA, no MutY. Bar 2, s.s. M13 DNA, plus MutY. Bar 3, d.s. M13 DNA, no MutY. Bar 4, d.s. M13 DNA, plus MutY.

FIG. 8B shows gel electrophoresis of the same DNA, and demonstrates that, in agreement with the chemiluminescence results in FIG. 8A, only single stranded M13 plus MutY demonstrate DNA digestion (see bands in Lane 2).

FIGS. 9A and 9B show detection of a mutation.

FIG. 9A shows chemiluminescence detection of a single mutation (A-to-C transversion) engineered in a p53 gene which is incorporated in a 7091 base pair plasmid. Plasmids containing the mutation were first digested into smaller DNA fragments (400–2.00 bp) by exposure to RSAI enzyme. These were then melted and hybridized with normal plasmids to form mismatches at the position of the mutation. The DNA was then enzymatically-treated with MutY to convert mismatches to aldehydes, BARP-labeled and captured on microplates. Bar 1, plasmid with mismatch, no MutY. Bar 2, plasmid with mismatch plus MutY. Bar 3, normal plasmid, no MutY. Bar 4, normal plasmid, plus MutY.

FIG. 9B shows the variation of the chemiluminescence signal obtained when different amounts of mismatch-containing plasmid treated by MutY and BARP are applied on microplates.

FIG. 10A demonstrates the binding of the compound, AED, (2-(aminoacetylamino) ethylenediamine) to reactive sites generated at position of mismatches in DNA by the enzyme MutY. The figure shows samples of M13 DNA containing mismatches, treated with enzyme and various compounds, stained with ethidium bromide and examined via gel electrophoresis. A sample of M13 DNA without enzymatic treatment shows a single bright band in lane A. The sample of plasmid DNA treated with the enzyme MutY shows multiple bands, demonstrating the expected recognition and cutting of mismatched bases by MutY in lane B. Lane C In Lanes C, D and E, the MutY treatments are carried out in the presence of 5 mM methoxyamine (C) or in presence of the novel compound AED (D, 5 mM and E, 10 mM AED respectively). The disappearance of the bands in lanes C, D and E is an indication of covalent high labeling of DNA by methoxyamine or by AED, at the positions of reactive sites generated by MutY. In Lane F, the treatment of DNA was as in Lanes E and D, but another aldehyde reactive compound (BARP) was used instead of AED. Lane F still shows the same multiple bands as those generated in the absence of compound (see Lane B), indicating an inefficient labeling of aldehyde sites by BARP.

FIG. 10B demonstrates the superior DNA binding of AED over BARP or FARP when reactive sites are generated at position of mismatches in DNA by the enzyme TDG. Lanes 1 and 2, G/T mismatch-containing oligonucleotide, no enzyme. Lane 3, G/T oligonucleotide with TDG enzyme. Lane 4, G/T oligonucleotide with TDG enzyme in the presence of 5 mM methoxyamine. Lane 5, G/T oligonucleotide with TDG enzyme in the presence of 5 mM BARP. Lane 6, G/T oligonucleotide with TDG enzyme in the presence of 5 mM AED. Lane 7, G/T oligonucleotide with TDG enzyme in the presence of 0.5 mM FARP.

DETAILED DESCRIPTION OF THE INVENTION

Figures 2A, 2B:
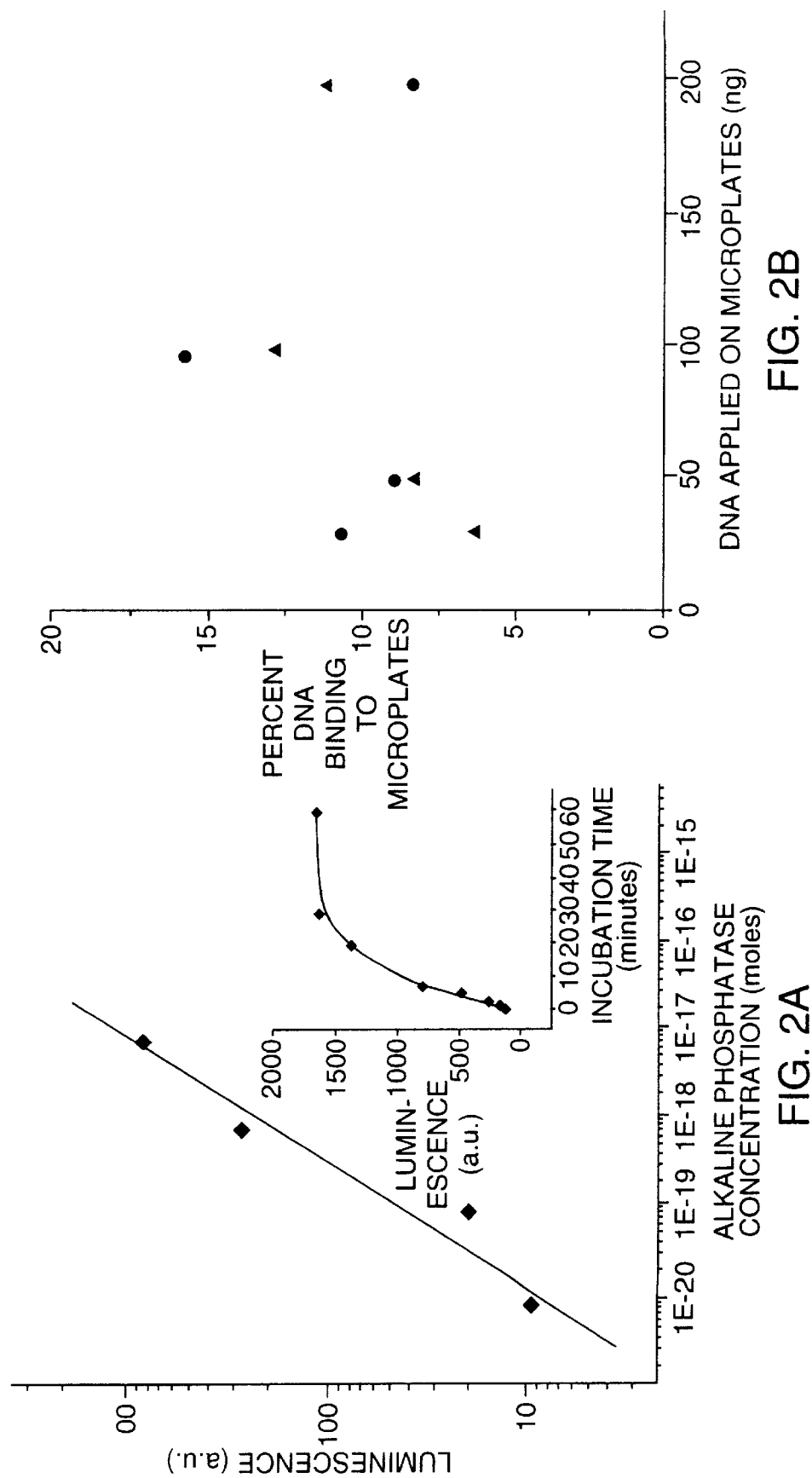
FIG. 2 shows the sensitivity of chemiluminescence detection of alkaline phosphatase with a cooled ICCD camera. The inset shows time-dependent buildup of chemiluminescence following addition of chemiluminescent substrate plus enhancer.

As described above, we have now developed a novel method that identifies genetic differences between two nucleic acid strands, thereby permitting the rapid identification of mutations in nucleic acids, e.g. DNA, or DNA segment(s). This method comprises (a) isolating the nucleic acid, e.g., DNA, to be screened for mutations (referred to as the target DNA), and hybridizing it with control DNA, to create mismatches. These mismatches occur at the exact positions of mutations or polymorphisms; (b) removing any pre-existing, spontaneous aldehydes by, for example, treating the DNA with hydroxylamine; (c) using repair glycosylase enzymes to convert the mismatches to reactive sites, namely, aldehyde-containing abasic sites (these enzymes recognize mismatches and will 'cut' the nucleic acid base, e.g., adenine at that site to create a reactive site); (d) using compounds (e.g. ligands) with functional groups that at one site can covalently bind to the reactive sites on the DNA, and that at a second site contain unique moieties that can be detected; (e) binding antibodies or avidin to the detectable second sites of the DNA-bound ligands. These antibodies or avidin may carry chemiluminescent or other indicators, so that the total reactive sites on the nucleic acid, e.g., DNA segment(s) tested is quantified, e.g. by chemiluminescence; (f) purifying the segments where a reactive site is present (e.g. by immunoprecipitation, or by ELISA-microplate-based techniques, or by microsphere-based techniques). The rest of the nucleic acid, e.g., DNA that does not contain mutations can then be discarded; (g) amplifying the remaining, mutation-containing nucleic acid, e.g., DNA, by PCR; and (h) analyzing that purified nucleic acid, e.g., DNA by standard gene-detection methods (e.g., hybridization), in order to find which gene each identified mismatch belongs to. Thereafter, by known techniques determining whether that mismatch is a mutation that either causes the disorder or is associated with the disorder or simply an allelic variation, i.e. a polymorphism.

The present method will recognize mismatches formed upon hybridization of the target DNA and the control (wild-type) DNA. Those skilled in the art are aware that mismatches may appear as a result of inherited or acquired genetic alterations. Also, that not every mismatch is the result of mutation but that some mismatches simply represent polymorphisms that occur naturally in populations. Both the inherited and the acquired genetic alterations in DNA will cause a mismatch.

Furthermore, those skilled in the art are aware that because all eukaryotic cells contain two copies of each chromosome, one paternal and one maternal, differences between the two alleles of each gene may also cause mismatches. In this case one gene copy (e.g. the paternal) will act as a control DNA and the second gene copy (the maternal) will act as the target DNA, and the mismatches will form upon hybridization of maternal and paternal DNA (i.e. simply by self-hybridization of DNA present in cells). These inherited differences can represent either polymorphisms or mutations.

There are a number of ways known in the art to distinguish whether a particular mismatch is an inherited polymorphism or mutation, or an acquired mutation.

One method that can be used to identify acquired mutations is to have the control DNA come from the same individual. For example, when screening a malignant cell the control DNA can be obtained from the corresponding non-malignant cell. By screening first the non-malignant cell alone and then the malignant cell (or a mixture of malignant and non-malignant cells) a comparison of detected mismatches in the two cases can be made. Differences that appear solely on the malignant cell and not on the normal cell comprise acquired mutations which may have lead to the malignancy.

When inherited (genetic) mutations/polymorphisms (i.e. where the alteration from the wild-type is present at birth and in every cell of the body) need to be identified, only normal cells need to be examined. As explained, inherited differences between the two alleles will cause mismatches upon self-hybridization. Detection of these mismatches will indicate the positions of inherited polymorphisms or mutations. Thereafter, one standard method to discriminate inherited polymorphisms from inherited mutations is to screen kindred and to determine whether or not the mismatch is present in normal kindred (i.e. a benign polymorphism) or only present in kindred showing a particular abnormality (i.e. a debilitating mutation).

The use of databases categorizing mutations and polymorphisms has also been increasingly popular. Thus, comparison of an identified genetic variation with those contained in a database can in many instances be used to determine whether the detected mismatch in DNA is due to a mutation or due to a polymorphism. One can also look at whether the mismatch causes truncation in the expressed protein.

Finally, another method that can be used to discriminate among mutations and polymorphisms is by the use of in-vivo assays. Thus, one can substitute a gene with at least one engineered base substitution mutation for the wild-type gene in an assay to determine whether or not the gene with the mutation can functionally replace a wild-type normal gene. If a gene can replace a wild-type normal gene in an assay and exhibit almost normal function that gene is not considered a mutation, but an allelic variation (i.e. polymorphism). If it cannot that gene will be considered a mutation.

One of the advantages of the present approach as opposed to mutation-detection methods presently being used is the ability to identify numerous mutations at diverse places in the genome. This permits one to determine if certain genes not presently associated with a particular abnormality may also have some relationship with that abnormality. For example, with hereditary non-polyposis colorectal cancer (HNPCC), mutations in the MSH2 and MLH1 genes are believed to be responsible for approximately 90% of the cases. A number of other genes have been identified as being responsible for the other 10% of the cases. However, in view of the cost of screening one typically looks primarily at MSH2 and MLH1. It may turn out when an array of genes are looked at the same time, that mutations in other genes also play a major role, in an individual with a particular condition. These other mutations may be associated with severity of the condition. By monitoring these additional genes and looking at disease state and recovery, one can develop a better idea of prognosis and treatment regimes than is currently available.

When using genomic DNA the skilled artisan is aware that numerous mismatches can and will occur in non-coding genetic regions. Looking at non-coding regions can permit the identification of mutations that affect expression and levels of expression. On the other hand when one is interested in looking for mutations in the expressed proteins it is preferable to use the mRNA to generate cDNA, and then form mismatches that can be detected by the present approach.

The present method permits biochemical approaches for chemically identifying the mismatch sites in, for example, the target DNA sequence. The target DNA can be identified by a detectable moiety and subsequently detected and purified by immunoprecipitation, microplates or microsphere technologies. Subsequently, the purified mutation-containing DNA fragments can be used in single-step screening of these mismatches by a wide variety of hybridization techniques (DNA chips, large-scale hybridization arrays, etc.)

For example, in trying to detect unknown mutations it has thus far proven difficult to screen for a single gene of about 8.5 kb (such as APC) in a single experiment, especially when an excess of normal alleles is simultaneously present [Sidransky, D. *Science* 278: 1054–1058 (1997)]. By contrast, the present method can screen several genes at once, and selects and isolates only those fragments containing a mutation/polymorphism. These mismatch-containing segments can be amplified by PCR and used, for example, in a DNA array to simply search for the matching gene(s) in the array to identify which genes these mutation-containing fragments belong to. Consequently, existing arrays for multiplexed gene expression scanning such as known in the art can be used. For example, Affymetrix Hu6800 DNA Chip, or the arrays described in [Wodicka, L. et al, *Nature Biotechnology:* 15: 1359–1367 (1997); Lockart, D. J. et al, *Nature Biotechnology* 14: 1675–1680 (1996); Schena, M.

Trends Biotechical 16:301–306 (1998): Yang, T. T. et al. Biotechniques 18: 498–503 (1995); Ginot F. *Human Mutation* 10: 1–10 (1997)].

In the present approach, in order to increase resolution (i.e. definition of the gene segment containing the mutation/polymorphism) the fragment should be smaller. However, in order to effectively prepare large amounts of mismatch-containing fragments by standard techniques such as PCR, the fragments should be at least about 50 bases. In some instances for ease of operation, a loss in resolution can be tolerated and larger fragments used.

Preferably the mismatch-containing fragment is 50–300 bases, more preferably 50–200 bases, still more preferably 50–100 bases and most preferably about 50 bases.

The nucleotides on the array (gene elements) should be between 8–300 bases preferably no larger than the size of the DNA of the mismatch-containing fragments. For improved resolution, smaller sizes should be used. For example, 50 bases or less, more preferably 8–25 bases. Many arrays presently available use nucleotide fragments of about 25 bases. Typically, these nucleotide segments are selected to be close to the 3' portion of the transcript.

However, other DNA arrays as discussed, infra, can also be used. Such arrays, which contain fragments that span the whole length of the gene (i.e. from both the 5' end of the gene as well as the 3' end) are preferred.

The preferred target nucleic acid is DNA. The DNA can be any mixture containing one or various sizes of DNA, such as cDNA synthesized from the whole mRNA collected from cells that need to be screened for mutation/polymorphism; or fractions thereof; or the whole genomic DNA collected from cells that need to be screened for mutation/polymorphism; or fractions thereof; or any combination of the above digested into smaller pieces by enzymes.

The control will be a wild-type fraction similar to the target. This wild-type likely will have no mutations. The control nucleic acid can be selected depending upon the intent of the test. For example, where acquired mutations in cancer cells are being screened, the control nucleic acid can come from a "normal" cell from the same individual. In other instances, for example, where an inherited (genetic) component may be involved the control DNA would come from a different subject than providing the nucleic acid; or simply differences among the paternal and maternal alleles can be examined by a self-hybridization of the DNA of the examined individual.

Following DNA isolation, the DNA is fragmented to reduce its size to the desired 50–300 base pairs, and generic PCR primers are added to the nucleic acids, in order to amplify the preparation at a later stage.

Thereafter in one embodiment, the target DNA is mixed and hybridized with wild-type DNA to create mismatches at the positions of differences, which are expected to be mutations/polymorphisms. The mixture is preferably treated with a compound such as hydroxylamine to remove any spontaneous aldehydes. Thereafter, the mismatches that occurred are recognized and converted to reactive sites (aldehydes) by enzymes such as a glycosylase repair enzyme such as MutY, and thymine DNA glycosylase (TDG) (e.g., from Hela cells or *E. coli*). A unique feature of these enzymes is that they are highly specific, i.e. they act only on mismatches while they leave non-mismatch containing DNA completely intact.

These reactive sites are identified by using a compound containing an aldehyde-binding moiety such as —O—NH2 (-hydroxylamine), or —NHNH2 (-hydrazine) or —NH2 (-amine) and also having a second moiety that reacts with a detectable entity (e.g. fluorescein, biotin, digoxigenin, which respectively react with antifluorescein antibody, avidin, and antidigoxigenin antibody. The antibodies may have chemiluminescence tags on them and thereby are detected). A unique feature of the present approach is that the aldehyde-binding moiety binds covalently to the enzyme-generated reactive sites. Combined with the specificity of the mismatch-repair enzymes, the use of covalently bound ligands to the position of mutations results in a sensitivity and specificity which is unparalleled by other methods for detection of mutations and polymorphisms.

The compounds have the general formula:

X-Z-Y, wherein

X is a detectable moiety, preferably X is $NH_2$, SH, $NHNH_2$, a fluorescein derivative, a hydroxycoumarin derivative, a rhodamine derivative, a BODIPY derivative a digoxigenin derivative or a biotin derivative;

Y is $NHNH_2$, O—$NH_2$ or $NH_2$, preferably Y is $NH_2$,

Z is a hydrocarbon, alkylhydroxyl, alkylethoxy, alkylester, alkylether, alkylamide or alkylamine. Z may contain a cleavable group (e.g. S—S). Z may be substituted or unsubstituted.

These reactive sites are identified by using a compound containing an aldehyde-binding moiety (Y) such as —O—$NH_2$ (-hydroxylamine), or —$NHNH_2$ (-hydrazine) or —$NH_2$ (-amine) and also having a second moiety (X) that reacts with a detectable entity (e.g. fluorescein, biotin, digoxigenin, which respectively react with antifluorescein antibody, avidin, and antidigoxigenin antibody. The antibodies may have chemiluminescence tags on them and thereby are detected). The aldehyde-binding moiety binds covalently to the enzyme-generated reactive sites. Combined with the specificity of the mismatch-repair enzymes, the use of covalently bound ligands to the position of mutations results in a high sensitivity and specificity.

One preferred embodiment of the invention has a general formula;

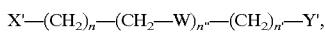

$X'$—$(CH_2)_n$—$(CH_2$—$W)_{n'}$—$(CH_2)_{n''}$—$Y'$, wherein $X'$ is $NHNH_2$ or $NH_2$, preferably $NH_2$;

$Y'$ is O—$NH_2$ or $NH_2$, preferably O—$NH_2$;

W is —NHC(O)—, —NHC(OH)—, —C(OH)—, —NH—, C—O—, —O—, —S—, —S—S—, —OC(O)—, or C(O)O—;

n is and integer from 0 to 12, preferably 4–7 and more preferably 6;

n' is an integer from 0 to 12, preferably 4–7, and more preferable 6, and n" is an integer from 1 to 4, preferably 1–2, and more preferably 1.

Preferably, the compound has a molecular weight between 100–500, more preferably 100–300, still more preferably 150–200.

Z and W can be substituted with groups that enhance the solubility of the resultant compound. Preferably the compounds of the formula X—$(CH_2)_n$—$(CH_2$—$W)_{n'}$—$(CH_2)_{n'}$—Y are overall soluble in the solvent used.

A preferred embodiment has the formula;

$$X''\text{---}(CH_2)_n\text{---}\underset{\underset{O}{\|}}{N}\text{---}C\text{---}(CH_2)_{n'}\text{---}Y''$$

§ wherein X", Y", n, and n' are as described as above.

A more preferred compound is 2-(aminoacetylamino) ethylenediamine (AED), (NH$_2$CH$_2$CH$_2$NHC(O)CH$_2$ONH$_2$).

2-(aminoacetylamino) ethylenediamine (AED)

In another prefered embodiment, the DNA reactive site recognized by enzymes such as glycosylases are identified by using compounds that contain a hydroxylamine reactive group. Examples of hydroxylamine compounds include FARP and FARPhc, both of which are fluorescent. FARP is a novel hydroxylamine containing derivative of fluorescein and FARPhc is a novel hydroxylamine containing derivative of hydroxycoumarin.

These compounds have the general formula;

$$X'''\text{---}(CH_2)_n\text{---}(CH_2\text{---}W)_{n''}\text{---}(CH_2)_{n'}\text{---}Y'''$$

wherein

Y''' is O—NH$_2$;

X''' is a fluorescent molecule, a fluorescein derivative or a hydroxy-coumarin derivative.

W, n, n', n" and n''' are defined as above.

More preferred compounds includes fluorescein aldehyde reactive probe, FARP, and fluorescent reactive probe hydroxycoumarin, FARPhc.

FARP

FARP$_{hc}$

DNA samples containing mismatches that are prepared and treated with DNA-glycosylase enzymes as described above, will form covalent oxime bonds to FARP and FARPhc.

In an alternative embodiment, the DNA reactive sites recognized by enzymes such as glycosylases are identified by using compounds that contain a hydrazine reactive group. An example of this class of compounds includes biotin hydrazine. The present invention allows using hydrazine compounds to label reactive sites generated by the DNA-glycosylase enzymes. In yet still another alternative embodiment, the compound is a biotin aldehyde reactive probe, such as BARP, a biotinylated derivative of hydroxylamine [BARP, Kubo K, Ide H, Wallace S S, and Kow. Biochemistry 31: 3703–3708, (1992)].

These biotinylated hydroxylamine or hydrazine compounds have the general formula;

$$X''''\text{---}(CH_2)_n\text{---}(CH_2\text{---}W)_{n''}\text{---}(CH_2)_{n'}\text{---}Y'''$$

wherein

Y''' is O—NH$_2$ or NHNH$_2$;

X'''' is a detectable molecule, biotin or biotin derivative.

W, n, n' and n" are defined as above.

For example, a Y moiety such as an amine should react with the aldehyde on for example the DNA, while the X group remains free for further modification and detection.

More preferred compounds includes biotin aldehyde reactive probe, BARP (BARP, Kubo K, Ide H, Wallace S S, and Kow. Biochemistry 31: 3703–3708, 1992) and biotin hydrazide:

BARP

It was discovered that, following the recognition of mismatches by glycosylases such as MutY or TDG, and the resulting conversion to aldehyde-containing reactive sites, the enzyme has to be kept inactive, otherwise it interferes with the subsequent covalent binding of the ligand compounds. As a result, the conditions for reaction of hydroxylamines, hydrazines or amines with the enzymatically-generated aldehyde-containing reactive sites are at temperature of 4° C.–15° C. and at pH 6–7. (In the specific case of Y=NH$_2$ (amines), the presence of a reducing agent such as borohydride, 4° C.–15° C. for 1–3 hours is also required during binding to reactive sites). Following covalent attachment of the ligand compounds to reactive sites, the enzyme is then inactivated via heating at 70° C., for 10 minutes. Alternatively, to remove the enzyme a standard phenol-chloroform extraction, or treatment with proteinase K can be adopted.

When X=NH$_2$ (amine), in order for the covalently-bound ligand to be recognizable by an antibody, the free —NH$_2$ group is first covalently linked to an amine-binding compound with a recognizable group (e.g. a succinimidylester compound such as biotin-LC-succinimidyl ester; biotin-LC-SS-succinimidyl ester [Pierce]; fluorescein-succinimidyl ester; etc.). The reaction and purification conditions of such succinimidyl esters with —NH2 containing compounds are well known.

When X=SH (sulfhydryl), in order for the covalently-bound ligand to be recognizable by an antibody, the free —SH group is first covalently linked to a sulfhydryl-binding compound with a recognizable group (e.g. a maleimide compound such as biotin-LC-maleimide; biotin-LC-SS-maleimide [Pierce]; fluorescein-aleimide; etc.). The reaction and purification conditions of such maleimides with —SH containing compounds are well known.

It was discovered that binding to reactive sites becomes much more efficient when small hydroxylamines (such as AED) are used. Therefore, the use of small compounds of the formula X'—(CH$_2$)$n$-(CH$_2$—W)$n''$-(CH$_2$)$n'$-Y , and of molecular weight less than 200 is preferred. These compounds are water soluble, can be incubated with DNA at a high molarity (e.g. 10 mM), and are able to diffuse fast enough to bind to reactive sites at a much higher level of efficiency than the other compounds (e.g. FARP, BARP) that have higher molecular weights and are less water soluble.

A major additional advantage of this invention is that the purification of the mismatch-containing DNA relies in the utilization of aldehydes as the recognition sites for mismatches combined with covalent bonding of the marker molecule to these aldehydes. Therefore, the presence of contaminating nucleases that cleave DNA and create 3' hydroxyl groups—containing strand breaks (—a common problem in similar assays—) do not generate binding sites for the marker molecules. Since the present method does not require the use of gel electrophoresis which compares DNA strand by their length or size, the generation of false positives from strand breaks generated by contaminating nucleases is thereby avoided. The method of the invention only detects labeled DNA following covalent binding of such aldehydes with ligand compounds and subsequent immobilization to a solid support, e.g., microplates. In addition, the length and diversity of DNA fragments are irrelevant to the assay, which is another advantage over gel-electrophoretic methods.

Once these compounds are covalently bound to the reactive sites, their reaction with a detectable group such as antibodies (e.g. avidin, antifluorescein etc.) and their subsequent detection (e.g. by chemiluminescence) and isolation (e.g. immunoprecipitation, avidin-coated microplates or microspheres, are well known in the art. For example, when X=NH2, direct immobilization and purification of the mismatch-containing DNA is possible on microplates coated with activated succinimidyl ester [Costar] or maleic anhydrite [Pierce] which covalently bind the NH2 group on the DNA-bound linker. When X=fluorescein, direct immobilization and isolation is achieved via antifluorescein-coated microplates [Boehringer]. And when X=biotin, direct immobilization and isolation is achieved via streptavidin-coated microplates (Pierce). In all cases, the immobilized DNA can be detected via alkaline-phosphatase or peroxidase-based chemiluminescence assays [see paper submitted to Nucleic Acid Research].

Those of ordinary skill in the art will recognize that a large variety of other possible detectable moieties can also be coupled to antibodies used to bind the DNA-coupled linkers at the positions of mismatches in this invention. Thereby providing additional methods to detect the antibody-bound mismatches on DNA. See, for example, "Conjugate Vaccines", *Contributions to Microbiology and Immunology,* J. M. Cruse and R. E. Lewis, Jr. (eds), Carger Press, New York, (1989).

The term "substituted," as used herein refers to single or multiple substitutions of a molecule with a moiety or moieties distinct from the core molecule. Substituents include, without limitation, halogens, hetero atoms, (i.e. O, S and N), nitro moieties, alkyl (preferably C$_1$–C$_6$), amine moieties, nitrile moieties, hydroxy moieties, alkoxy moieties, phenoxy moieties, other aliphatic or aromatic moieties. Preferably the aliphatic or aromatic moieties are lower aliphatic or aromatic moieties, i.e. 12 or less carbons, more preferably 6 or less carbon atoms. Substituted compounds may be referred to as derivatives of the core structure.

Antibodies of the present invention can be detected by appropriate assays, such as the direct binding assay and by other conventional types of immunoassays. For example, a sandwich assay can be performed in which the receptor or fragment thereof is affixed to a solid phase. Incubation is maintained for a sufficient period of time to allow the antibody in the sample to bind to the immobilized labeled DNA on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized labeled DNA of the present invention is subsequently incubated with labeled antibody or antibody bound to a coupling agent such as biotin or avidin. Labels for antibodies are well-known in the art and include radionucleotides, enzymes (e.g. maleate dehydrogenase, horseradish peroxidase, glucose oxidase, catalase), fluorophores (fluorescein isothiocyanate, rhodamine, phycocyanin, fluorescamine), biotin, and the like. The labeled antibodies are incubated with the solid and the label bound to the solid phase is measured, the amount of the label detected serving as a measure of, for example, the amount of anti-FARP antibody present in the sample. These and other immunoassays can be easily performed by those of ordinary skill in the art.

The present method allows for extremely sensitive mismatch-scanning in diverse DNA fragments, thereby resulting in sensitive and high throughput mutation screening over several hundreds or thousands of genes at once. For example, it becomes possible for the screening and discovery of novel mutations in tumor samples which is instrumental to establish the pathogenesis of cancer and to establish new relations between mutations and cancer or other diseases. The new compounds and methods described above are also useful in analysis of the genetic background (polymorphisms, mutations) of any individual. These new compounds and methods may also be used for high throughput genotyping and genotypic selection.

One can use DNA chips to identify the gene where the mismatch is present. For example, the Affymetrix Inc. (San Diego, Calif.) HU6800 DNA chip; the Clontech Atlas™ DNA array (Palo Alto, Calif.); the Telechem International array (San Jose, Calif.); the Genetix Ltd. array (Dorset, UK); and the BioRobotics Ltd. array (Cambridge, UK). The chip such as the Affymetrix DNA chip contains densely-packed DNA or RNA elements. For highest resolution the oligomers on the chip should be small. Preferably 8–50 nucleotides, more preferably 8–25 nucleotides. This will provide the highest resolution. However, the DNA or mRNA on the chips can be as large as the mismatch-containing DNA fragments, e.g. 50–300 nucleotides.

For example, using a conventional array, (e.g., the Affymetrix chip for detecting gene expression) the array will have multiple DNA or RNA elements densely packed, each comprising 25-mer oligonucleotides immobilized on a solid support. For each of the 6,800 genes which are represented on the chip, there are 20 elements each containing 25-mer oligonucleotides with a distinct portion of the mRNA sequence. Thereby the 20 elements 'sample' the mRNA sequence of the gene. In the current chip version, the immobilized probes are biased towards the 3' end of the mRNA, thus sequences towards the 5' end are not well represented. To use the array for detecting gene expression, users generate cDNA from the genes to be screened in the test sample (typically 1 $\mu$g) and then perform in-vitro transcription to collect cRNA and biotinylate it (~50 $\mu$g), 12 $\mu$g of which are hybridized on the chip (alternatively, cDNA can directly be applied on the chip without in-vitro transcription). If a gene is present in the test sample, then it hybridizes to an appropriate array element. Because the array is constructed to contain known gene sequences at known positions, all the transcribed genes are detected in a single step. The detection process utilizes addition of a marker-identifier such as a fluorescent scanner. The magnitude of the signal from each element signifies the degree of gene expression for the specific gene.

It should be noted that the present invention utilizes the same arrays but not anymore to detect gene expression (i.e. difference in signal among array elements), but mutations, which requires only detection of presence or absence of signal (indicating polymorphism/mutation in the specific gene fragment which was captured), thereby making the detection task much simpler.

Inherited single nucleotide polymorphisms (SNPs) and mutations can define a genetic predisposition towards several diseases, including cancer, cardiovascular, neurodegenerative and others. Indeed, acquired SNPs, mutations and loss of heterozygocity are particularly pertinent to cancer development, and early cancer detection. All of the above can be simultaneously detected in a single step by the above-described methodology.

For example, cDNA for tumor and normal issue of a single individual is prepared. (See FIG. 12) Because inherited polymorphisms is a frequent event (average 1 SNP per 1000 bases), several genes will have more than one SNP. Also, the tumor genes will contain one or more inherited SNPs as well as occasional acquired SNPs/mutations. Next, the cDNA is digested by enzymes down to small fragments (~100–200 bp), thereby generating fragments that are likely to contain only one—or none—genetic alternations. Then, each sample is melted and self-hybridized, to generate mismatches at positions of SNPs/mutations. The above-described methodology using an X-Z-Y compound is applied as described above, to isolate only the mismatch-containing cDNA.

The mismatch-containing cDNA is PCR-amplified, labeled, e.g. biotinylated, and applied on a chip such as the Affymetrix chip: Each mismatch-containing fragment will hybridize to its complementary oligonucleotide on the array, thereby revealing which gene and which gene region (to within 100–200 base pairs) the SNP/mutation belongs to. By comparing arrays A and B, both the inherited and the acquired SNPs/mutations can be derived. Loss of heterozygocity may occur when an acquired SNP/mutation occurs in the same gene with an inherited SNP/mutation. Such genes can readily be identified by comparing A and B.

Current arrays, including the Affymetrix chips, because they are intended for detection of gene expression, they utilize immobilized oligonucleotides which are biased toward the 3' end of mRNA. Accordingly, the 5' end of the gene is underrepresented and therefore will miss all the mutations that are towards the 5' end of the genes. Therefore, although the combination of the present methodology with the existing DNA chips allows mutation scanning over several sections of the genome (which is currently impossible by other methods), the mutation scanning is restricted towards the 3' end of the genes. By contrast, our methodology combined with new DNA chips (infra) makes it possible to identify mismatches over complete sections of the genome.

A preferred Mutation Scanning Array should contain immobilized oligonucleotides, preferably 8–25 bases long, which span the whole mRNA sequence of each gene represented on the array, and not biased toward one or the other mRNA end. As mentioned, the oligonucleotides can be larger, but by increasing size, resolution is lost. The oligonucleotides should sample the mRNA in intervals not bigger than the DNA fragments isolated by present method preferably 50–100 bases but capable of ranging from 20–300 bases In this manner the mismatch-containing fragment will be assured of finding a complementary sequence on the array. When immobilized oligonucleotides on the array are arranged to sample the mRNA at small intervals (e.g. 20 bases) there will be redundancy of information upon hybridization of the mutant fragments to the DNA chip, as each fragment may simultaneously hybridize to two or more immobilized oligonucleotides. In this case, by using the combined information from all array elements, a better resolution of the position of the mutation will be achieved.

This Mutation Scanning Array can be constructed using the same technologies as for the current arrays. The described modification will allow SNPs/mutation detection over the whole length of the immobilized genes to be identified. The immobilized genes can be either the whole genomic cDNA library, or an arbitrary fraction of that, or a specific collection of genes that are known to be related to a specific disease (i.e. disease specific arrays).

A major advantage of the present mutation scanning chip technology is that it can detect SNPs/mutations in the presence of an excess of normal alleles in the initial sample because the methodology first isolates the mutants, and the array subsequently identified the gene. This is currently impossible to do with existing technology.

A preferred kit will comprise reagents to isolate mRNA from tissues, synthesize cDNA, fragment DNA to 100–200mers and add PCR primers, form heteroduplexes, use MutY and TDG enzymes to cut the mismatches, remove spontaneous aldehydes, apply the X-Z-Y compounds e.g., FARP/BARP/AED, to detect mismatches, and isolate mutant fragments by immobilization on microplates, recover and PCR mutants, and finally apply on an array to detect SNPs/mutations at specific genomic positions.

The kit can be used to screen an individual for inherited susceptibility to cancer, cardiovascular disease, neurodegenerative disorders, etc. by mapping positions of heterozygocities and SNPs in the whole genome or in selected fractions of the genes.

The present methodology also permits one to detect early onset of cancer (acquired SNPs/mutations) from tissue biopsies or excretions. The present technology also permits research labs to detect new mutations and correlate them to other diseases.

The ligand compounds described demonstrated excellent detection of DNA mismatch-repair recognition sites. In addition, based on our discovery that small (MW<200–250) compound allow high binding efficiency (>50%) to DNA reactive sites, new compounds (like AED) were designed, synthesized and tested. These were shown to bind reactive sites generated by MutY much more efficient than compounds of higher (>250) molecular weight. These new compounds are unique in that they are small, water soluble, do not encounter significant steric interactions with DNA and can diffuse fast to the enzymatically-generated reactive sites on DNA. This class of new bifunctional compounds is also uniquely designed to retain their water solubility as the chain length is extended. The simultaneous addition of internal polar functional groups along with methylene groups maintains the water solubility of these compounds in spite of the increased length of the molecule. Care must be taken however to retain a low overall molecular weight for the final compound. Useful polar functional groups include; alcohols, esters, ethers, thioethers, amines and amides. This allows users of this method the flexibility to tailor the chain length of the compounds to suit their specific needs with out the loss of water solubility, which is essential.

In one method which aims to map base substitution mutations in tumor samples, mRNA is isolated from a malignant cell. The corresponding mRNA from a healthy or normal tissue sample is also isolated. The mRNA from the normal tissue will serve as the wild-type control. A cDNA library can be made for each mRNA sample, the cancerous and wild-type. The two cDNA libraries are added together, for example in a 1:1 ratio and hybridized. (See FIG. 1) The hybridization produces a mixture of double stranded DNA. The double strands of DNA that consist of cDNA from the malignant cell hybridized with a strand of wild-type DNA will now typically contain some mismatches that are associated with the malignancy.

The mixture of hybridized cDNA is then treated with hydroxylamine to remove any spontaneous aldehydes, and then the hydroxylamine is removed via G25 filter centrifugation of the samples. The double stranded cDNA which is now void of pre-existing aldehydes, is then treated with a mismatch-repair glycosylase, such as MutY or TDG. MutY is a DNA-repair enzyme that recognizes mismatched adenosine nucleotides, and TDG recognizes mismatched thymines. Upon recognition, MutY or TDG remove the base by cleavage at the point of attachment to the deoxyribose sugar. Removal of the base by this method of cleavage results in the opening of the deoxyribose ring with formation of an aldehyde. Since pre-existing aldehydes were removed by hydroxylamine treatment, the only aldehydes are those generated at positions of mutations.

The resulting strands of cDNA now contain an aldehyde located at each point of mismatch. These resulting aldehydes are then treated with one of the compounds, e.g. the 2-(aminoacetylamino)ethylenediamine (AED) or one of its analogues, at low temperature so that further activity of the MutY/TDG enzymes is suppressed. The DNA labeled with AED is then selectively immobilized on microplates as described earlier in this text. The unlabeled DNA is then washed away leaving behind only AED labeled DNA attached to the microplate. The DNA with the labeled mutations, while immobilized on the microplates is then biotinylated and the mutations can be detected, for example, via chemiluminescence. Mutation-containing DNA can then be recovered from microplates for identification of the genes involved via PCR and large-scale hybridization techniques which are established in the field of molecular biology. Consequently, all mismatch containing genes are captured at once and the number of genes that can be simultaneously screened is only limited by the total genes the DNA array can handle. To verify and identify the exact position of the mismatche(s) on each particular gene identified by the present invention, conventional procedures such as sequencing can be used.

In another embodiment, the fluoresceinated compound FARP can be used instead of AED. FARP-labeled DNA is immobilized on microplates, isolated from unlabeled DNA and the total number of mismatches may be detected by a sensitive photon-detecting technique, e.g. fluorescence or chemiluminescence. The mismatch containing DNA is subsequently recovered from the microplates for identification of the genes containing mismatches. This may be performed in a single step by large-scale hybridization procedures on DNA arrays.

This method can also be used to detect a variety of other DNA lesions that are converted to reactive sites by glycosylase enzymes or by chemical means (e.g. clustered DNA-damaged sites); abasic sites; carcinogen-DNA adducts; damaged DNA bases). In these embodiments, mixing of for example the target DNA with wild-type DNA to create mismatches is not needed. Enzymes will recognize damage and will generate reactive sites directly in the target DNA. Such enzymes include all known glycosylases, such as endonuclease III, T4 endonuclease V, 3-methyladenine DNA glycosylase, 3- or 7-methylguanine DNA glycosylase, hydroxymethyluracile DNA glycosylase, FaPy-DNA glycosylase, M. Luteus UV-DNA glycosylase. Also, chemical agents such as bleomycin, alkylation agents or simple acid hydrolysis can generate reactive sites automatically in target DNA without any enzyme. The crucial step however is again the same, i.e. covalent addition of compound to the reactive site of the DNA lesion, which allows subsequent sensitive detection.

The described technology can be used for mutation screening and for research. For example, the use of solid supports at every stage of the assay will substantially shorten the time required to screen tumor samples, improve its cost-effectiveness in terms of man-power as well as its reliability and reproducibility.

For instance, magnetic microsphere technology can be utilized to immobilize heteroduplexes at an early stage of the assay. Following mRNA extraction from e.g., a host cell such as cancerous and normal samples, cDNA for e.g. 588 genes can be generated. Thereafter PCR primers that contain a cleavable (S—S) biotin are added. Hybridization of the cancerous cDNA with wild-type alleles generates heteroduplexes at the positions of base substitution mutations, and the DNA sample is immobilized on, for example, the streptavidin-coated magnetic microspheres (available from Dynal Inc.). From this point onwards, all subsequent steps of the ALBUMS assay can be conducted on the solid support.

The microspheres allow chemical/enzymatic treatment of the immobilized DNA and efficient, rapid separation of chemicals from DNA via magnetic immobilization of the microspheres during washing. For example, in one embodiment the assay uses hydroxylamine treatment to remove traces of aldehydes and subsequent complete removal of hydroxylamine via repeated (×3) ultracentrifugation through G25 filters. This can be time-consuming and result in an inevitable loss of sample, which can be important when tissue samples are limited. In contrast, by immobilizing the DNA magnetic microspheres, all subsequent steps become faster, easier and without DNA loss: Hydroxylamine treatment and removal, enzymatic treatment and washing, X-Z-Y treatment and washing, binding antifluorescein-AP to e.g. AED-trapped mismatches and washing, and finally chemiluminescent detection of mismatches are performed on the magnetic microsphere format.

Alternatively, to recover the DNA from magnetic microspheres and isolate the X-Z-Y, e.g. FARP, containing DNA, instead of adding antifluorescein-AP the immobilized DNA can be recovered by cleaving the disulfide (S—S) bond on the biotin by mild exposure to a reducing reagent (DTT, 50 mM, ~10 min, 25° C.).

To construct primers end-labeled with a cleavable moiety such as biotin, oligonucleotides containing a terminal aliphatic amine are ordered, and reacted with e.g. a biotin —S—S-succinimidyl ester (available from Pierce). Reactions of succinimidyl ester with amino-oligonucleotides and subsequent purification by reverse C18 column chromatography are standard procedures on which our group has had prior experience.

Following removal of DNA samples from the magnetic microspheres, the samples will be applied on e.g. antifluorescein-microplates to isolate e.g., FARP-containing heteroduplexes which subsequently will be recovered, PCR amplified and screened on the Clontech DNA hybridization array. Using the above procedures, base substitution mutations can be isolated via ALBUMS, amplified by PCR and screened on the DNA array in less than 24 hours. Thus, this technique results in a standardized procedure with easy access to researchers and clinicians for cost-effective, large-scale mutation screening of a target sample, such as cancer samples.

In one embodiment, kits for carrying out the identification of these DNA mismatches can be sold. The kits would include the repair glycosylase, an X-Z-Y compound and preferably instructions. These materials can be in any vial. The materials can be in lyophilized form.

In a preferred embodiment, PCR primers would also be included.

In one preferred embodiment the following kit materials and instructions can be included:

Kit Formulation

1. Isolate target and control cDNA. Fragment DNA to 100–200mers by standard enzymes.
2. Add PCR primers that contain a cleavable biotin at the end.
3. Mix target with control, cross-hybridize.
4. Bind sample to streptavidin-coated magnetic microspheres. (alternatively, streptavidin-coated microplates can be used).
5. With the sample immobilized on solid support, perform: hydroxylamine treatment/washing; MutY/TDG treatment(s)/washing; FARP/BARB/AED labeling/washing. Antibody labeling/washing; Chemiluminescence detection of mismatches. All these steps are very easy and convenient to perform with the DNA immobilized.
6. To recover sample and isolate the mutation-containing DNA, add DTT (see below) to break the S—S bond on the cleavable biotin.
7. Now apply the preparation on an appropriate solid support for the ligand compound chosen: (antifluorescein, streptavidin, succinimidyl-ester-coated plates for FARP, BARP and AED respectively). Remove unbound DNA, capture only mutated DNA.
8. Now collect mutated DNA from microplates. This can be done by several methods; e.g. adding 1 M of hydroxylamine to break the bond between the ligand and the DNA; or raising the temperature to denature captured DNA and collect the unmodified strand; or, in the case of cleavable —S—S-containing probes, simply add DTT to break the bond to the microplate.
9. Apply PCR using the primers inserted in step 2.
10. Detect mutated genes using hybridization techniques.

All documents mentioned herein are incorporated herein by reference.

The following examples are illustrative of the invention and are not limitations thereon.

EXAMPLE 1

Method for Large-Scale Detection of Base-Substitution Mutations in Cancerous Samples, Using One of the X-Z-Y Compounds, the FARP Marker Molecule (See FIG. 1)

Isolated mRNA from a cancerous tissue is transcribed into cDNA. Primers can be added to DNA at this stage for PCR amplification at a later stage (see FIG. 1). The sample is then hybridized with a corresponding wild-type sample of DNA to generate mismatch pairing at the positions of mutations. The hybridized DNA is treated with hydroxylamine to remove any aldehydes that may have formed spontaneously. The hybridized DNA sample is then treated with the MutY enzyme. Enzyme treatment recognizes A/G mismatches and upon recognition, depurinates the DNA and simultaneously generates an aldehyde at the site of mismatch. The DNA is then treated with the labeling compound AED or FARP or BARP to generate a covalent oxime bond at the position of the mismatch. Upon labeling, the DNA is immobilized on microplates appropriate for the specific labeling compound and excess, unlabeled DNA is washed away. The DNA labeled at mismatch sites can now be analyzed by a variety of methods including detection of total mutations by chemiluminescence or identification of labeled genes via DNA arrays.

Materials and Methods

1) DNA, oligomers and chemicals

FARP [5-(((2-(carbohydrazino)methyl)thio)acetyl)-aminofluorescein, aminoxyacetyl hydrazide, Fluorescent Aldehyde Reactive Probe] was synthesized as described (Makrigiorgos G M, Chakrabarti S and Mahmood S. Int J Radiat Biol, 74: 99–109, 1998). High purity genomic calf thymus DNA and double stranded ladder (pUC18 Msp I digest, 27–500 base pairs) was purchased from Sigma Chemical and used without further purification. Single stranded (+strand) M13 DNA was purchased from Pharmacia Biotech and pGXIs14 plasmid DNA, a gift from Professor MacLeod, MD, Anderson Cancer Center, was isolated from the host bacteria as described earlier (Makrigiorgos G M, Chakrabarti S and Mahmood S. Int J Radiat Biol, 74: 99–109, 1998). Both agarose gel electrophoresis and the absorbance ratio at 260 nm to 280 nm were performed to determine the purity of the plasmid. Gel-purified 49-mer oligonucleotides representing the TFIIIA transcription factor-binding sequence of the Xenopus rRNA gene (enumerated in Table 1, at the end of this Example) were supplied by Oligos Etc Inc. Enzyme MutY (*E. coli*) was purchased from Trevigen Inc. and stored as recommended by the manufacturers. Hydroxylamine purchased from Sigma Chemical was already freshly made prior to the experiments. GTG agarose was obtained from FMC Bioproducts, polyacrylamide gel electrophoresis reagents were from National Diagnostics while SYBR GOLD nucleic acid gel stain and Picogreen™ DNA quantitation dye was supplied by Molecular Probes. For chemiluminescence studies, Reacti-Bind NeutrAvidin coated polystyrene plates (pre-blocked with Bovine Serum Albumin) were supplied by Pierce. Anti-fluorescein-Fab fragments (Sheep)-alkaline phosphatase conjugate (antiF-AP) was purchased from Boehringer Mannheim. CDP-Star, a 1, 2 dioxetane chemiluminescent enzyme substrate and Emerald-II™ enhancer used with CDP-star was purchased from TROPIX. Micro Bio-Spin G25 chromatography columns were obtained from Bio-Rad laboratories. Label IT™ Nucleic Acid biotinylation kit was purchased from PanVera Inc. All reagents and buffers were of analytical grade and made with ultrapure water (1800 Mohm m$^{-1}$ resistivity) delivered by an Alpha-Q system (Millipore).

2) Acidic or physiological depurination of calf thymus DNA. Treatment with hydroxylamine Aldehyde containing apurinic/apyrimidinic (AP) sites were chemically induced in calf thymus or plasmid DNA by a short exposure (0–60 seconds) to acidic conditions (pH=3.5) over a set time period at a temperature of 38° C., as described (Makrigiorgos G M, Chakrabarti S and Mahmood S. Int J Radiat Biol, 74: 99–109, 1998). The reaction was halted by placing the sample quickly on ice and adding a neutralization solution (10% of 3M sodium acetate and 1M potassium phosphate buffer at pH 7 and 7.5 respectively), to final volume of 50 μl. AP sites were also slowly generated in calf thymus DNA via spontaneous depurination at 37° C., pH=7.0, over a period of days, and these were monitored with the present assay. Prior to incubation at 37° C., the DNA was treated with 5 mM hydroxylamine for 1 hour at room temperature to remove traces of existing aldehydes from the pool of potential FARP-binding sites. The hydroxylamine was then removed via G25 ultracentrifugation and the sample was resuspended in sodium phosphate buffer, pH 7.

3) FARP-trapping of aldehydes and subsequent DNA biotinylation

To covalently trap open-chain aldehydes generated in DNA at the position of AP sites, 500 μM FARP was reacted with 0.05–2.5 μg of DNA in 40 mM sodium citrate pH 7.0 at 15–22° C., for 30 minutes. Non-covalently bound FARP was removed by G25 ultracentrifugation. FARP-labeled DNA was either used on the same day or stored at 4° C. or −20° C. for a few days, prior to further experiments. To immobilize FARP-labeled DNA on neutravidin microplates, the DNA was exposed for one hour to a commercially available biotinylation reagent (Biotin Label IT™ reagent, 1 μl; reagent per μg DNA, in MOPS buffer, pH 7.5 at 37°). Excess reagent was them removed by G25 ultracentrifugation. The samples were either used immediately or stored at 4° C. for a few days, prior to chemiluminescent studies.

4) Chemiluminescence measurement of FARP-trapped aldehydes in calf thymus or plasmid DNA Double stranded DNA, doubly labeled with FARP and biotin, was immobilized on neutravidin-coated microplate strips in the presence of 5 nM antiF-AP. 30–50 ng of doubly labeled DNA plus 5 nM antiF-AP in a total of 50 μl was incubated at room temperature for one hour in TE pH 7.5. Unbound sample and antiF-AP were removed by pipeting and washing with TE at least four times. The microplate strips were then transferred in to 50 ml polypropylene tubes and washed four times in 30ml–50 ml of TE buffer with constant agitation for 10 minutes. The chemiluminescent substrates (CDP-Star plus Emerald II enhancer) were then added in 0.1 M diethanolamine, pH 8.5 and the anti-F-AP-catalyzed reaction was carried out at room temperature for 1 hour, after which maximum light generation was achieved. In separate experiments, to quantitate the fraction of biotinylated DNA captured on microplates Picogreen™ dye was used to measure double stranded DNA just prior and after its removal from neutravidin-coated plates.

5) Chemiluminescence Instrumentation

The low light from the chemiluminescence reaction was detected using an intensified charged coupled device (ICCD) system (Princeton Instruments). This ICCD camera utilizes a proximity focused microchannel plate (MCP) image intensifier, fiber-optically coupled to the CCD array. The entire area of the ICCD is capable of light detection, giving a total of 576×384 pixels on a Pentium® PC computer screen. Both the intensifier and CCD are cooled to −35° C. thermoelectrically and the dark current is less than 50 counts per minute. The ICCD was used to detect total light generation from each cell of the microplate strip. Cells were individually placed in a reproducible geometry at −2 mm distance from the ICCD and the total light output per second measured. The background chemiluminescence (signal measured when FARP was omitted from the procedure) was subtracted from all samples. All measurements were repeated at least three times.

6) Formation of homoduplex and heteroduplex oligonucleotides 49-mer oligonucleotides and their complementary strands with or without a centrally located T-to-G base substitution were synthesized. In another synthesis of the same oligomers, 5' biotinlyated 49-mers and their complementary unbiotinylated strands were synthesized (Table 1). For hybridization, equimolar amounts (~0.5 μg) of each oligonucleotide were annealed in 40 mM Tris-HCl (pH 7.5), 20 mM MgCl$_2$ and 50 mM NaCl to form duplex oligonucleotides. The mixture was first heated to 95° C. for 2 minutes, then allowed to hybridize at 65° C. for 3 hours and cooled slowly to room temperature. Following hybridization, the double stranded 49-mers were treated with hydroxylamine (5 mM in citrate pH 7.0, for 30 minutes, 25° C.) to remove traces of spontaneously or heat-generated aldehydes from the pool of FARP-reactive sites.

7) Treatment of M13 DNA, ladder DNA and duplex oligonucleotides with MutY and TDG and gel electrophoresis 50 ng of the test DNA (single stranded M13, ladder DNA, or duplex oligonucleotide were incubated for 1 hour, 37° C. with 1.0 unit MutY in 40 mM Na-citrate buffer (pH 7.0) and then alkali treated to concert positions of missing adenine to strand breaks. Analysis of cleavage products for single stranded M13 DNA was done by agarose gel electrophoresis 0.9% agarose, run overnight at 20 V in 1× TBE buffer and stained with 1 μg/ml ethidium bromide). Fragment analysis for ladder DNA and oligonucleotides was done by 16% denaturing polyacrylamide gel electrophoresis in the presence of 7.5M urea at 20 V/cm. The DNA fragments were detected by SYBR Gold dye or by ethidium staining and photographs taken by Eagle Eye™ Still Video (Stratagene).

8) Chemiluminescence measurement of FARP-trapped mismatches in oligonucleotides, ladder and M13 DNA M13 DNA, ladder DNA, or 5'-biotinylated oligonucleotide duplexes, hydroxylamine-treated, were exposed to MutY, FARP-labeled biotinylated with the protocols described above. The biotinylation step was omitted for the oligonucleotides since these were pre-biotinylated In some experiments, samples were kept at 70° C. for 8 minutes to inactivate the enzyme at this stage. Typically 50 ng from the doubly (biotin plus FARP) labeled nucleic acids were applied on neutravidin-coated microplates and their chemiluminescence measured.

Results

1) Dual labeling of DNA and chemiluminescence detection using the present protocol FIG. 2 shows chemiluminescence obtained with the present setup when serial dilutions of free alkaline phosphatase were added to CDP-Star® substrate and Emerald II enhancer and measured using the cooled ICCD. The chemiluminescence detection limit of this set up is less than 0.01 attomoles alkaline phosphatase. Examination of the buildup of alkaline phosphatase chemiluminescent signal in solution following mixing with substrate plus enhancer at room temperature, demonstrates that after 60 minutes a relatively constant value is achieved (FIG. 2, inset). Therefore all measurements reported were conducted 60–80 minutes following addition of the substrate. To estimate the fraction of biotinylated DNA captured on the neutravidin-coated microplates, biotinylated DNA was quantitated using the fluorescence of Picogreen™ dye prior to its application and immediately following removal of unbound DNA from microplates (not shown). 49-mer oligonucleotides resulted in approximately 10% capturing on the plates while of the 50–100 ng high molecular weight calf thymus DNA less than 2% was immobilized on the plates, possibly due to secondary structures and associated steric hindrances.

2) Ultrasensitive detection of aldehydes in DNA

Figure 3:
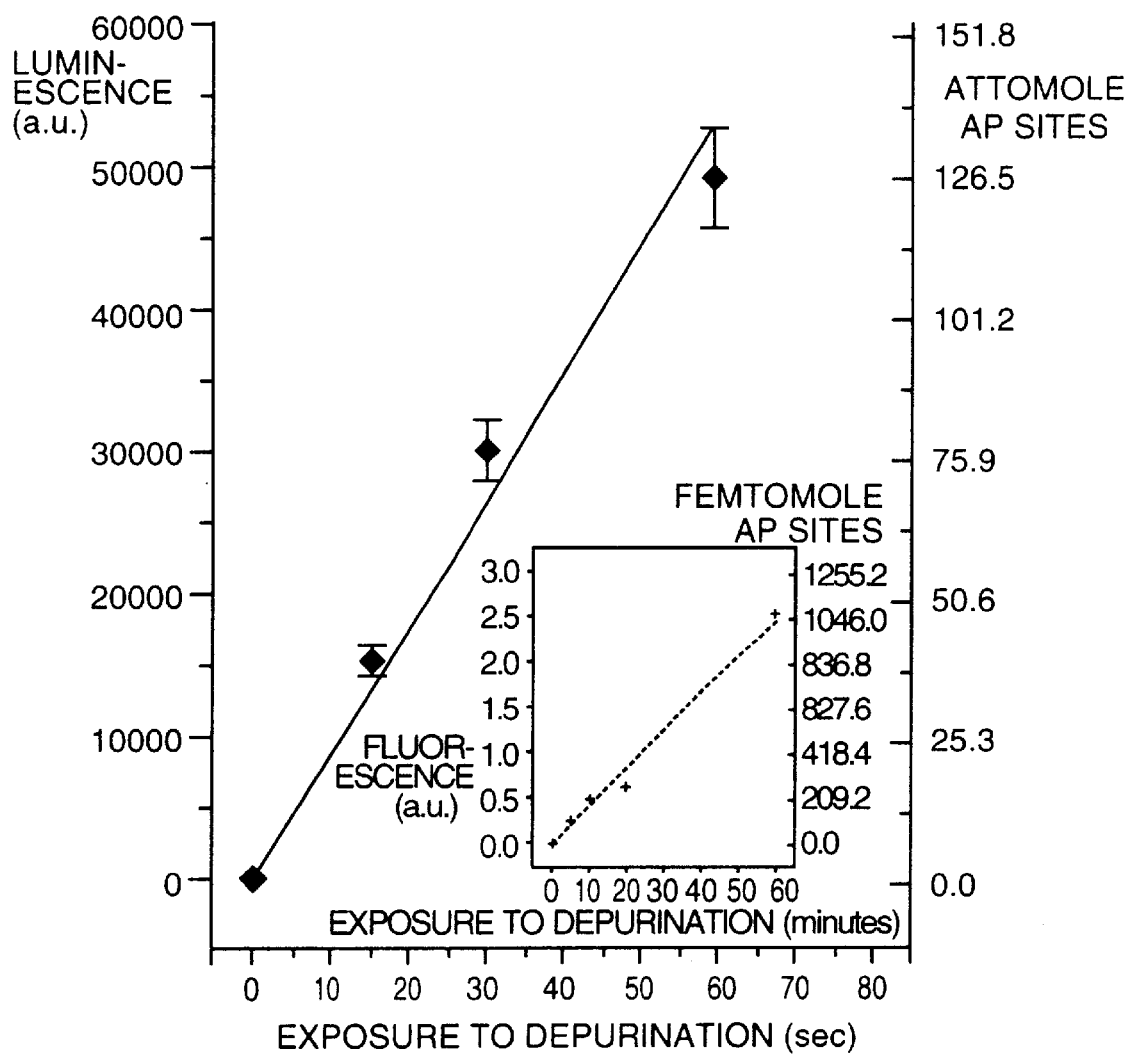
FIG. 3 shows chemiluminescence detection of aldehyde-containing apurinic/apyrimidinic (AP) sites generated in plasmid DNA following depurination in sodium citrate, pH 3.5 at 38° for up to 60 seconds. The inset depicts fluorescence detection when extensive depurination under identical conditions is applied. Data in the inset (from us (Makrigiorgos G M, Chakrabarti S and Mahmood S. Int J Radiat Biol, 74: 99–109, 1998) were used to convert chemiluminescence units to AP sites (right axis, see text).

Chemiluminescence detection of aldehyde-containing AP sites generated in 100 ng plasmid DNA following depurination in sodium citrate, pH 3.5 at 38° C. for up to 60 seconds and trapping of AP sites by FARP is depicted in FIG. 3. The induction of luminescence is linear with respect to depurination exposure. The inset, from an earlier work (Makrigiorgos G M, Chakrabarti S and Mahmood S. Int J Radiat Biol, 74: 99–109, 1998), demonstrated detection of fluorescence following FARP-labeling of this same plasmid exposed under identical conditions to higher depurination times (0–60 minutes). The fluorescence-based approach is less sensitive than the present method, however, it allows direct quantitation of the number of FARP molecules per DNA base pair. Five minutes depurination under the same protocol yields approximately 1 AP site per 34,000 bases (Makrigiorgos G M, Chakrabarti S and Mahmood S. Int J Radiat Biol, 74: 99–109, 1998). Assuming a linear decrease of AP sites for lower depurination exposures, the 15 second exposure in FIG. 3 corresponds to approximately 1 AP site per $7 \times 10^5$ bases. The amount of microplate-captured DNA generating this signal is approximately 1–2 ng. Therefore the absolute number of AP sites recorded following 15 seconds depurination is approximately 5 attomole (see right axis in FIG. 3).

Figure 4A:
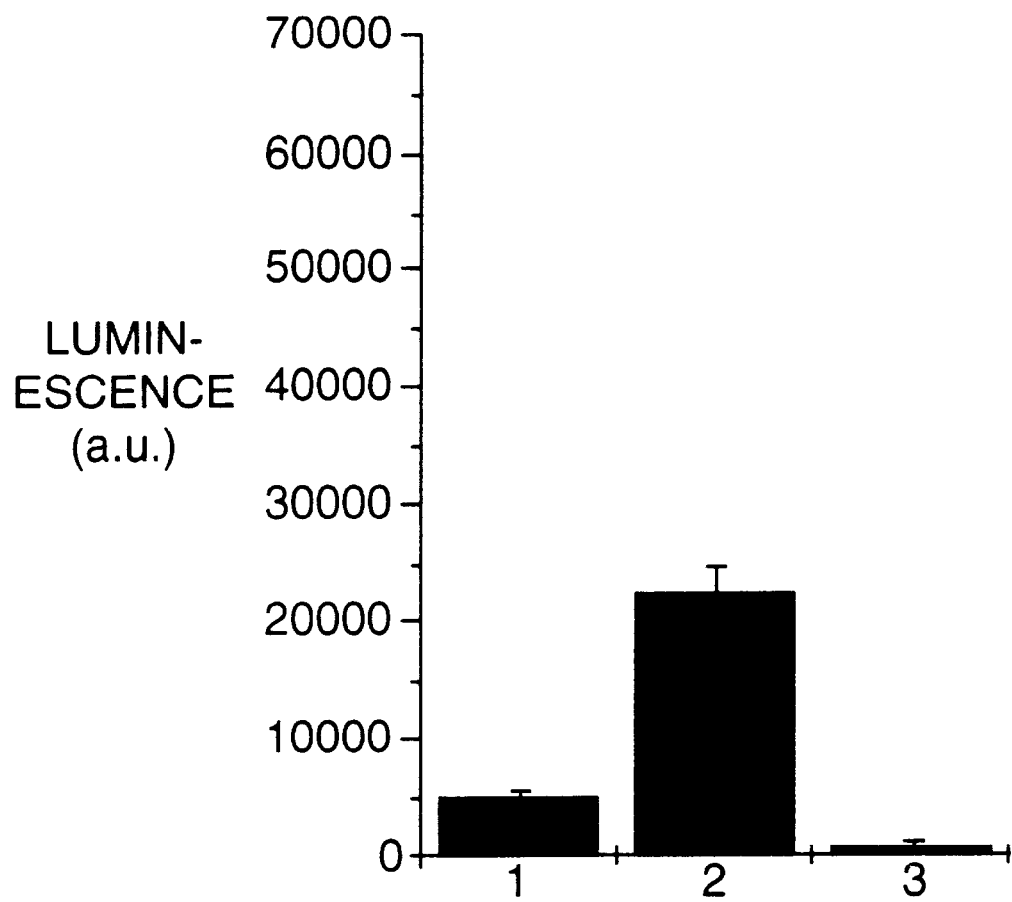
FIGS. 4A and 4B shows sensitive detection of AP sites using FARP.
Figure 4B:
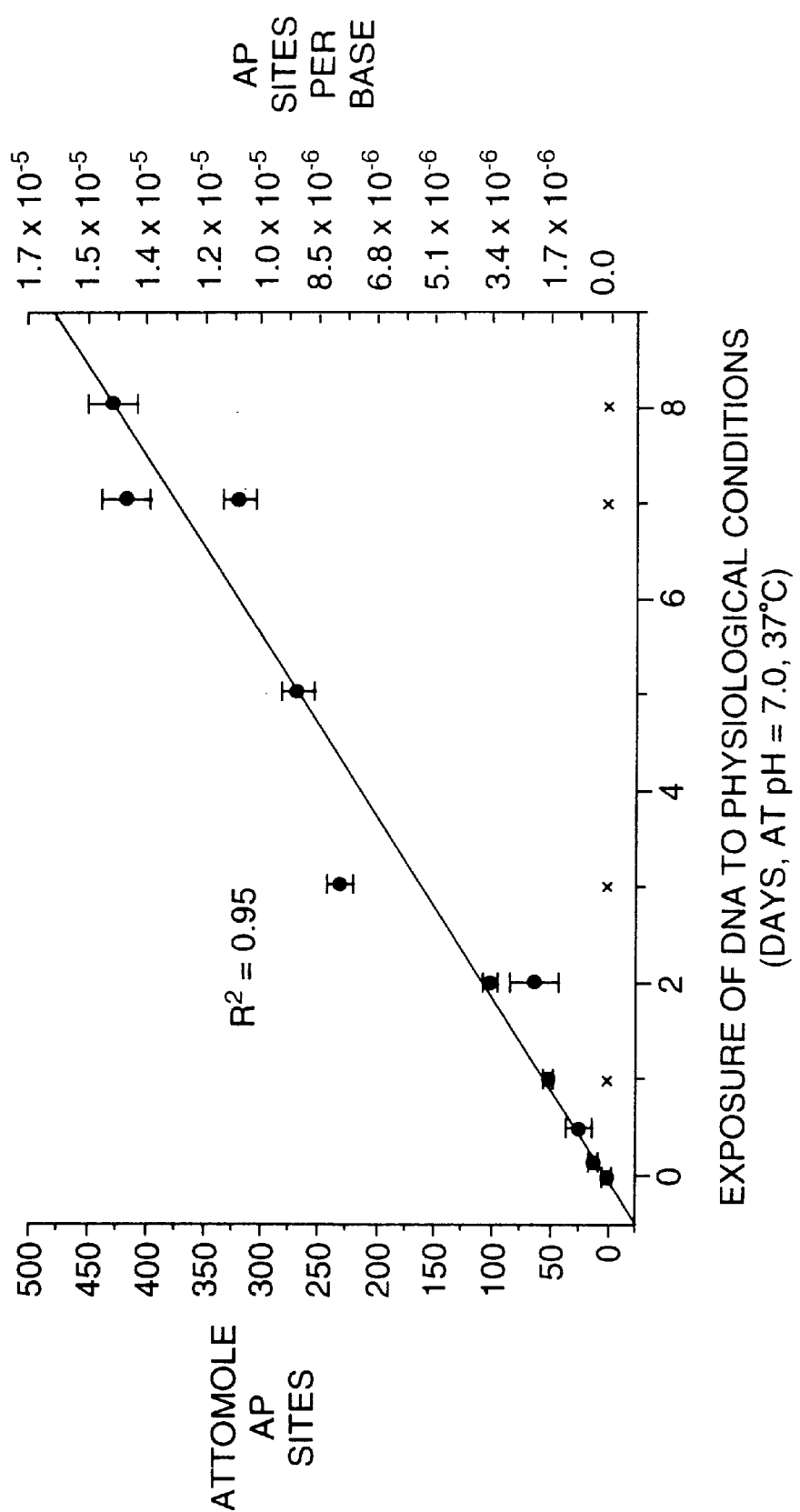

To estimate the lowest number of AP sites detectable, hydroxylamine treatment of genomic calf thymus DNA was first employed in order to remove traces of spontaneously-generated AP sites (e.g. AP sites expected to be present in genomic DNA from mammalian cells prior to DNA extraction plus AP sites generated during handling). Hydroxylamine is a small molecule and is expected to react rapidly with aldehydes, as previously demonstrated for methoxyamine (Talpaert-Borle M, and Liuzzi M. Biochimica Biophysica Acta, 740: 410–416, 1983), thereby prohibiting subsequently added FARP to react at the same positions. FIG. 4A depicts the decrease in the chemiluminescence signal obtained following hydroxylamine treatment of genomic calf thymus DNA depurinated for 15 seconds. Following hydroxylamine removal and reaction with FARP, the chemiluminescence was reduced to almost background levels. When hydroxylamine-treated calf thymus DNA was kept at 37° C., phosphate buffer pH=7, and assayed for AP sites via FARP as a function of time, a linear increase in spontaneously-generated aldehydic AP sites was detected (FIG. 4B). DNA kept at 4° C. under similar conditions did not display any luminescence signal (FIG. 4B). According to FIG. 4B, the limit of detection by the present microplate-based method is ~0.2 attomole AP sites, or 1 AP site per $2 \times 10^7$ bases, using a starting DNA material of about 100 ng.

Figure 5A:
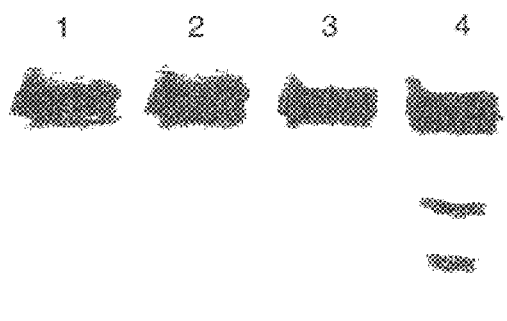
FIGS. 5A–5C shows gel electrophoresis of MutY-treated DNA, examined on denaturing gels.
Figure 5B:
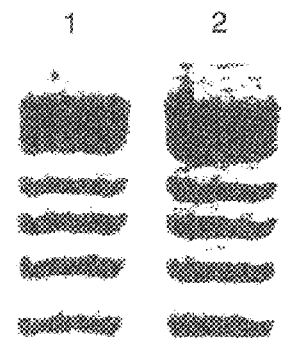

3) Gel electrophoresis of MutY-treated oligonucleotides and single stranded M13 DNA 49-mer oligomers engineered to form a double stranded structure, with or without a centrally located A/G mismatch upon hybridization, were exposed to MutY, alkali treated and examined upon denaturing gel electrophoresis. Generation of the two expected fragments was observed for the heteroduplex oligomers, while no cutting as present in the homoduplexes (FIG. 5A). Under the conditions applied, the fragmented DNA appears to be less than 50% of the total DNA per lane, which would result if all A/G mismatches were reacted upon by MutY. The homoduplex-containing double stranded DNA ladder (27–500 base pair fragments) did not demonstrate additional fragmentation following enzymatic treatment (FIG. 5B). In contrast, MutY treatment of the 7249 base-long M13 single stranded DNA resulted in the generation of approximately 6 fragments, the largest of which is about 1000 bases long, as demonstrated in lane 5, FIG. 4C. Generation of MutY-recognized sites in the single stranded high molecular weight DNA is attributed to sequence self-complementation generating transient mismatches. It can be inferred that, to generate 6 discrete fragments, and assuming a less than 100% efficiency of MutY in cutting each site, an average of 3 MutY-recognized cutting sites are generated per each 7249 base-long M13 molecule.

Figure 5C:
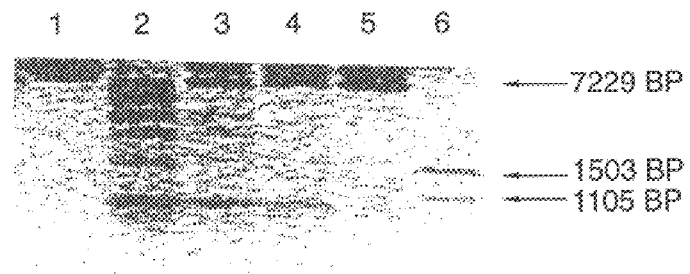
Figure 6:
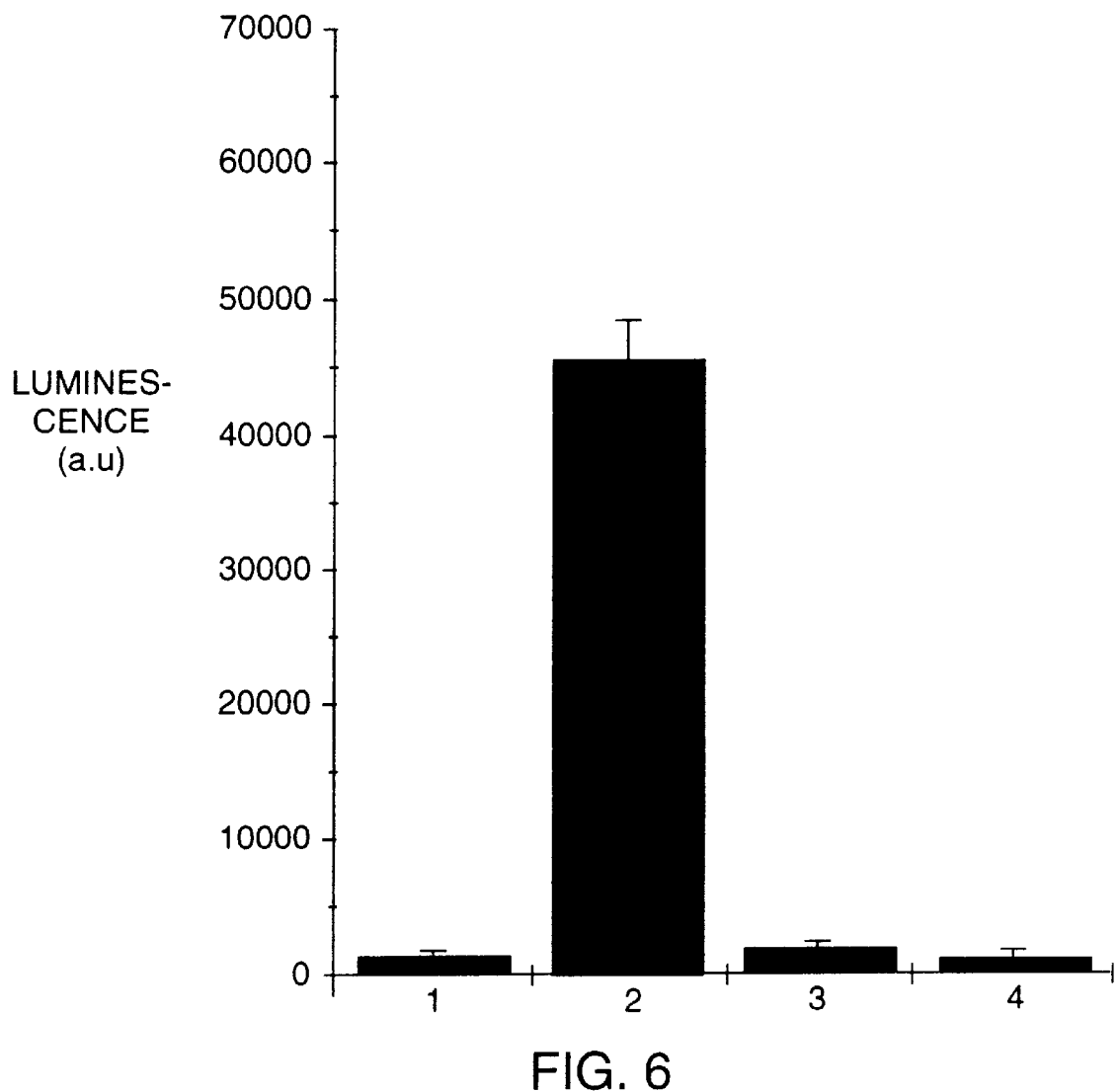
FIG. 6 shows FARP-based chemiluminescence detection of MutY-treated DNA of a single length: 49-mer oligonucleotides are enzymatically-treated, FARP-labeled and captured on microplates. Bar 1, A/G mismatch, no MutY. Bar 2, A/G mismatch, plus MutY. Bar 3, No mismatch, no MutY. Bar 4, no mismatch, plus MutY.
Figure 7:
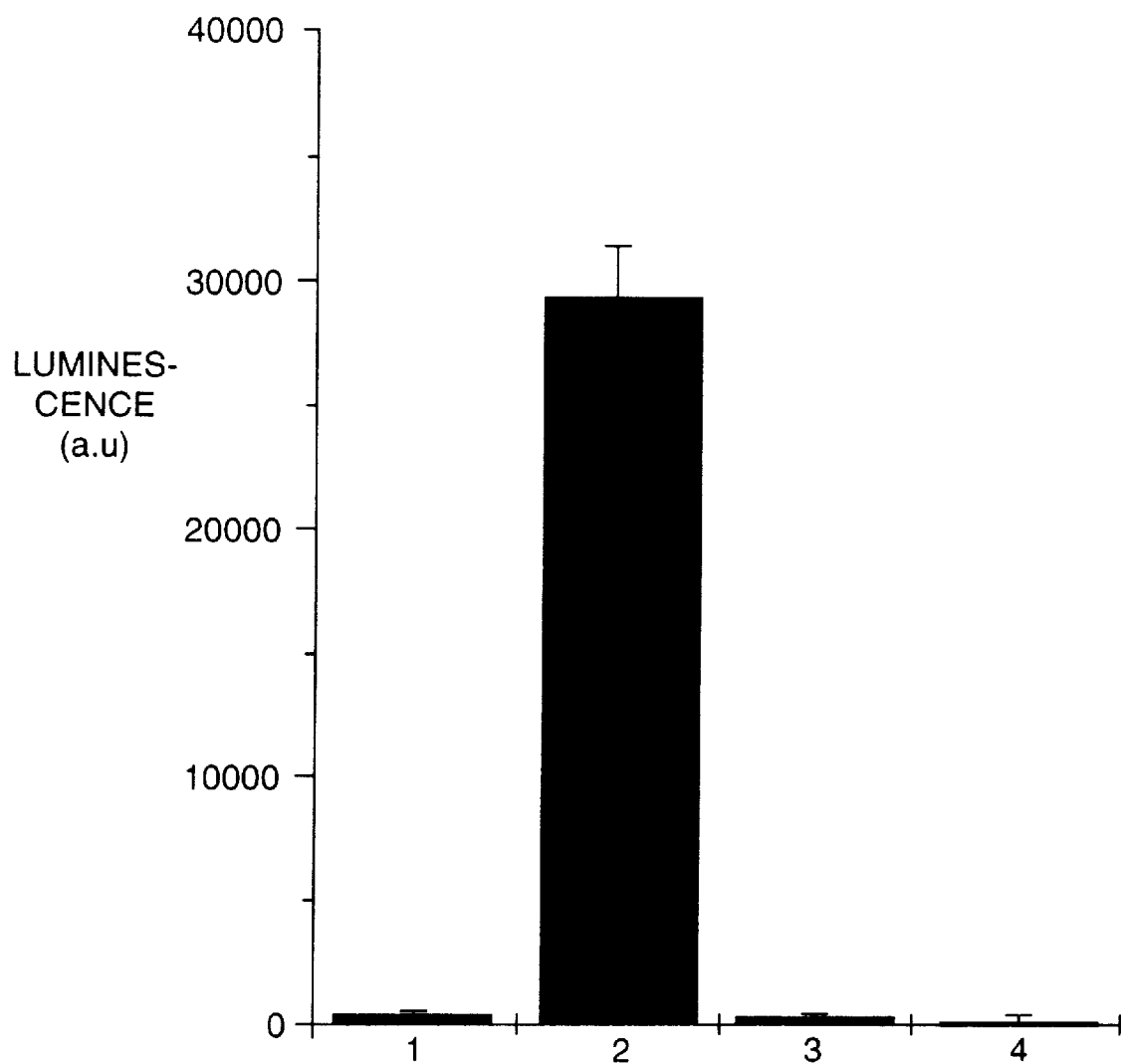
FIG. 7 shows FARP-based chemiluminescence detection of MutY-treated DNA fragments of varying length: Single stranded M13 DNA (7249 bases) and double stranded homoduplex mixtures (DNA ladder, 27–500 base pairs) are enzymatically-treated, FARP-labeled and captured on microplates. Bar 1, M13 DNA, no MutY. Bar 2, M13 DNA, plus MutY. Bar 3, ladder DNA, no MutY. Bar 4, ladder DNA, plus MutY.

4) FARP-based chemiluminescence detection of mismatches in high and low molecular weight DNA Starting with 100 ng of biotinylated 49-mer homoduplexes or heteroduplexes, the nucleic acid was treated successively with hydroxylamine, MutY, then FARP and applied on neutravidin microplates for chemiluminescence detection of mismatches. A strong signal was obtained for A/G mismatch-containing oligonucleotides (FIG. 6), while no signal was obtained when MutY was omitted, or when oligonucleotides without mismatch were MutY-treated. A mixture of double stranded homoduplexes (DNA ladder) treated in the same way also demonstrated absence of chemiluminescence signals (FIG. 7). In contrast, single-stranded M13 demonstrated a chemiluminescence signal of about 100 times the signal obtained without MutY indicating the generation of FARP-reactive sites following MutY treatment (FIG. 7). The chemiluminescence results agree with the fragmentation results obtained by gel electrophoresis (FIG. 5).

TABLE 1

Sequences of the synthesized oligonucleotides

1. B-5'-GTC TCC CAT CCA AGT ACT AAC CAG GCC CGA CCC TGC TTG GCT TCC GAT T-3' (SEQ ID NO:1)

2. B-5'-AAT CGG AAG CCA AGC AGG GTA GGG CCT GGT TAG TAC TTG GAT GGG AGA C-3' (SEQ ID NO:2)

3. B-5'-AAT CGG AAG CCA AGC AGG GTA GGG CCT GG__C__TAG TAC TTG GAT GGG AGA C-3' (SEQ ID NO:3)

1 and 2 are complementary and form a homoduplex. 1 and 3 form a heteroduplex with an A/G mismatch at position 20. On a separate set of oligonucleotides, a biotin molecule (B) was incorporated at 5' end during synthesis.

EXAMPLE 2

BARP-Based Detection of Mismatches Formed via Self-Complementation of Single-Stranded M13 DNA

Figure 8A:
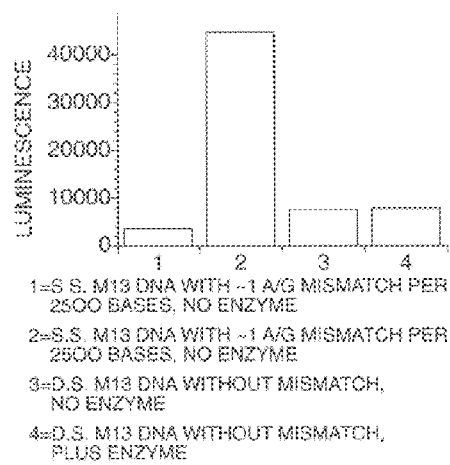
FIGS. 8A and 8B show BARP-based chemiluminescence detection of MutY-treated DNA fragments of varying length.
Figure 8B:
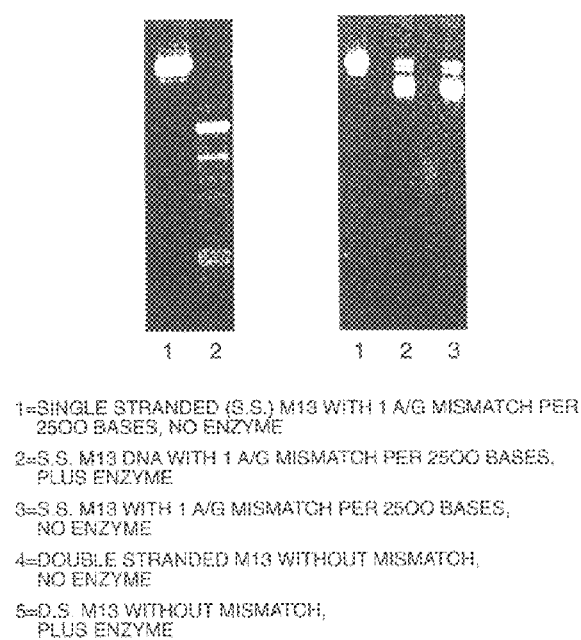

Samples of M13 single stranded DNA that contain approximately 1 MutY-recognizable mismatch per 2,500 bases were treated with MutY to generate aldehyde-containing reactive sites appropriate for reaction with BARP. Nominal gel electrophoretic studies as well as BARP-based chemiluminescent studies were then preformed. Control samples used were: Single stranded M13 without enzymatic treatment; Double stranded M13 DNA without any mismatches and no enzyme treatment; and double stranded M13 DNA without mismatches and enzyme. FIG. 8 (A and B) shows the results of both methods of detection. FIG. 8A (luminescence studies) show that only when mismatches are present (single stranded M13) and MutY is used is there a chemiluminescence signal. In agreement, gel electrophoresis (FIG. 8B) shows cuts in M13 are only generated under the same conditions. It can be seen that there is good agreement among the two methods. As described, the method is highly specific for mismatch-containing DNA, i.e. DNA without mismatches, or DNA with mismatches but no MutY generate no signals.

EXAMPLE 3

Detection and Isolation of DNA Containing Base-Substitution Mutations: Detection of a Single A-To-C Transversion Engineered in a P53 Gene within a 7091-Long Plasmid

The ability of the present technology (A.L.B.U.M.S) to detect base mismatches (demonstrated in previous examples) is directly applicable to detection of base substitution mutations. For example, a standard procedure to generate mismatches at the positions of mutations in DNA, is to mix mutation-containing DNA with wild-type DNA. Upon heating and re-hybridization of the mixture, heteroduplexes with mismatches are generated at the positions of mutations (FIG. 1), which can then be detected with high sensitivity and specificity as demonstrated in example 1.

To isolate mutation-containing DNA from normal DNA, following BARP-labeling of the generated aldehydes at positions of mismatches (FIG. 1) the DNA is immobilized on neutravidin-coated microplates, followed by exhaustive washing to remove the homoduplex DNA. As a result, only BARP-containing DNA is retained on the plates, thereby isolating mutant DNA.

To recover the purified mutation-containing DNA from the microplate, the samples can be either heated 2 min at 96° C. or treated 1 min with NaOH to denature the DNA and recover the non-covalently modified strand, which is then used for amplification via PCR. The following section detail the procedure.

A 7,091 bp long plasmid that incorporates the full-length human cDNA p53 sequence (1,691 bp) was engineered to contain base subsitutions, via site-specific mutagenesis. The present technology was used to detect a known A-to-C base substitution mutation engineered in codon 378 within the plasmid-incorporated p53. Circular plamids (1 µg) containing mutant p53 genes were treated with a 5'-CG/CG-3' cutting enzyme (BstU I, Sigma, 1 unit, 1 h, 37° C.) to generate linear fragments (~400 to 2,500 bp), followed by a 10 minute, 70° C. treatment to inactivate the enzyme. The mutant-containing sample (1 µg) was mixed (1:1) with a similarly treated normal p53-containing sample, heated (96° C., 2 minutes) and hybridized overnight, at 65° C. to generate A/G (25 %), and T/C (25 %) mismatches at p53 codon 378, as well as homoduplex p53 and plasmid fragments.

To detect the presence of the mutation via ALBUMS, 100 ng of the mismatch-containing DNA mixture (p53 plus plasmid fragments) was treated exactly as described for the M13 treatment in example 2: (a) hydroxylamine treatment and removal, (b) MutY treatment and BARP-binding, (c) fluoresceination and (d) binding to neutravidin plates and chemiluminescence detection. FIG. 9A demonstrates that strong signals are observed when the mutation is present, while background signals are obtained from normal p53-containing plasmid (i.e. complete lack of false positives). FIG. 9B shows variation of signals versus DNA amount applied on microplates. These data represent an average of 4 independent experiments.

In conclusion, the present technology (A.L.B.U.M.S) allows a sensitive and specific detection of 1 base substitution mutation within a 7,091 bp-long, p53-containing plasmid with a virtual absence of false positives (defined as signal when no mismatch is present, FIG. 9A). Unequivocal detection of a single base substitution within a 7,091-long plasmid cannot easily be conducted with any of the existing methodologies (Nollau P and Wagener C. *Clinical Chemistry* 43: 1114–1128, 1997). The present method on the other hand can detect the mutation on a microplate with minimal sample (<100 ng) and effort involved. Following formation of heteroduplexes, the procedure is currently completed in 6 hours, requires no special equipment or laborious handling and can be automated on microplates so that 96 samples can be examined at once. To achieve a similar result using conventional sequencing would not be possible (Primrose S B, Principles of Genome Analysis, Chapter 5, Sequencing Methods and Strategies, p125, Second Edition, Blackwell Science Ltd., Oxford, UK).

EXAMPLE 4

Comparison of Small Versus Large Ligand Compounds in Binding to MutY- or TDG-Generated Reactive Sites in DNA: Synthesis and Advantage of AED Versus BARP and FARP. Chemiluminescence Signals by AED.

(a) To synthesize AED, O-(Carboxymethyl) hydroxylamine hydrochloride was conjugated to ethylenediamine (Aldrich) in distilled water using 1-Ethyl-3-[3-(dimethylamino)propyl] carbodiimide (EDAC) as the coupling reagent. An 100-fold excess of ethylenediamine over O-(Carboxymethyl)hydroxylamine hydrochloride was utilized during the reaction to allow preferential coupling of ethylenediamine to the carboxyl groups. The conditions for the catalysis of this reaction by EDAC is well known to those skilled in the art. TLC analysis and purification on silica gel with $CHCl_3:CH_3OH:CH_3COOH$ in a 70:20:5 ratio indicated the product at an $R_f$ of 0.2–0.25. The certificate of analysis provided 1H NMR data consistent with the AED structure provided earlier.

Figure 10A:
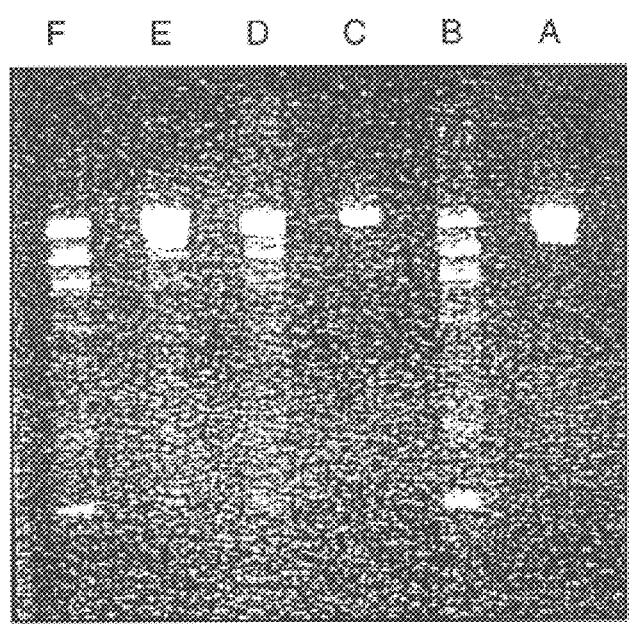
FIGS. 10A and 10B compare DNA binding by different compounds.
Figure 10B:
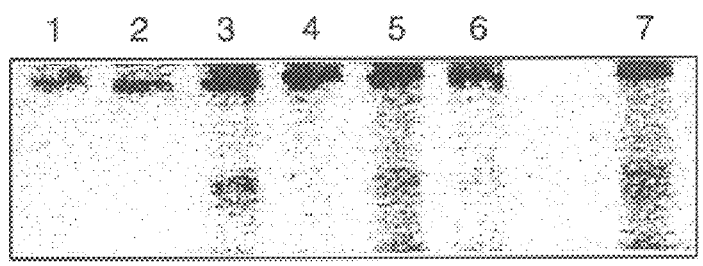
Figure 11:
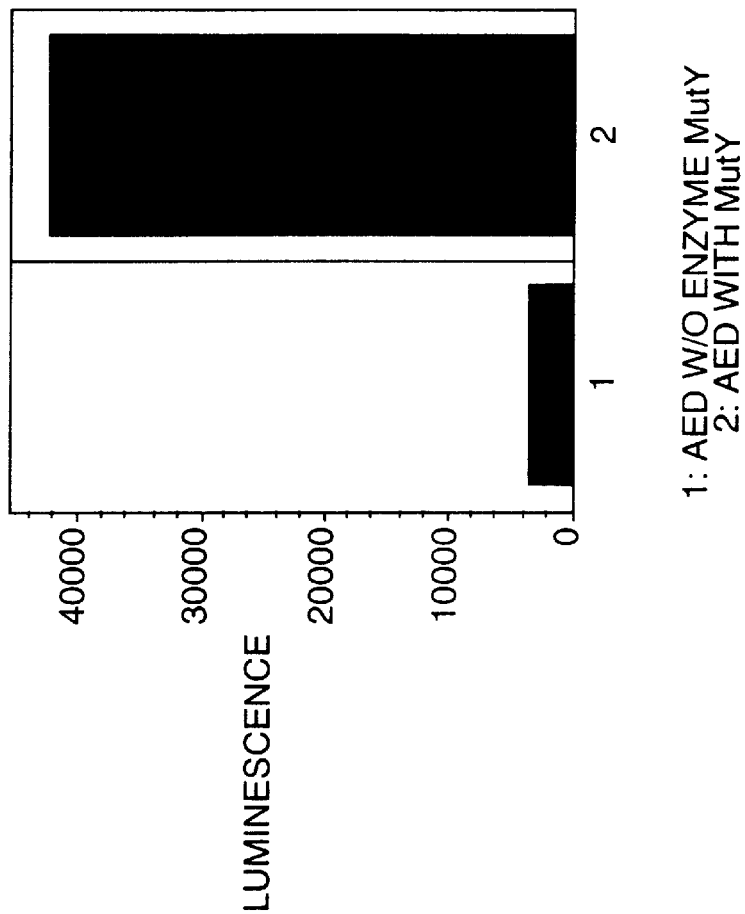
FIG. 11. AED-based chemiluminescence detection of mismatches obtained when mismatch-containing s.s. M13 DNA is MutY treated in the presence of 5 mM AED. Bar 1, M13 DNA without MutY enzyme. Bar 2, M13 DNA with MutY enzyme.

(b) The ability of hydroxylamine-based compounds (e.g. FARP, AED, BARP, or methoxyamine) to bind reactive sites in DNA can be tested with a simple experiment. It is well known that, if hydroxylamine-compounds (such as methoxyamine) are covalently bound to aldehyde-containing abasic sites in DNA, then treatment with alkali (NaOH) cannot generate a strand break at the position of base loss (—otherwise a cut is generated). This simple observation allows direct testing of ligand binding to DNA following MutY-treatment of the nucleic acid (FIG. 10A) or TDG-treatment of nucleic acid (FIG. 10B). Mismatch-containing single-stranded M13 DNA was subjected to MutY to generate aldehyde containing abasic sites, and then alkali-treated to generate fragments at the positions of mismatches. Lane 2, in FIG. 10A (agarose gel stained with ethidium bromide and photographed under UV light) demonstrates the generated fragments. In lanes 3, 4, 5, and 6, during MutY incubation the following ligand compounds were also included: 5 mM methoxyamine, 5 mM AED, 10 mM AED or 5 mM BARP respectively. As expected, the very low molecular weight compound methoxyamine prevents formation of any fragments, indicating a 100% binding to all reactive sites formed. Also, AED (bands D and E) demonstrates an almost complete binding to the reactive sites, especially when 10 mM is used (Lane E). In contrast, BARP can only prevent to a very small degree the formation of bands, indicating a very low (<5%) binding affinity to the reactive sites. Similarly, in FIG. 10B, the TDG enzyme was used (TDG recognizes mismatched thymine and generates an aldehyde at that position following excision of thymine). Oligonucleotides with a G/T mismatch were synthesized (lanes 1, 2, oligos alone) and exposed to TDG in the absence (lanes 3) or in the presence of 5 mM methoxyamine (lane 4), 5 mM BARP (lane 5), 5 mM AED (lane 6) or 0.5 mM FARP (lane 7). It can be seen that the cuts generated by TDG (lane 3 lower band) are not present when methoxyamine (lane 4) or AED (lane 6) are included in the reaction, demonstrating the binding of these compounds to the mismatches. BARP and FARP on the other hand (lanes 5 and 7) demonstrate significantly lower binding, since the lower band is present.

In conclusion: (a) AED is almost as efficient as methoxyamine (100%) in binding the MutY-generated reactive sites. (Methoxyamine itself however cannot be used in the present application because, unlike AED, following binding it allows no further derivatization as it has no secondary binding site available for antibody binding). (b) BARP only shows little (<5%) binding; despite that, and because the present method is extremely sensitive, high chemiluminescence signals are still generated with BARP when mismatches are present, as shown in the previous example. The same is valid for FARP.

The ability of DNA-bound AED to be recognized by a secondary ligand and then by an antibody, as described in the Detailed Description section of this invention was demonstrated by the following. The free primary amine (—NH2 group) of AED was covalently bound to biotin by addition of 1 mM biotin-LC-succinimidyl ester (Pierce) in 0.1 M sodium bicarbonate, pH=8.5 for 2 h. The conjugate was purified by ultracentrifugation through 2 G25 filters (Pharmacia), fluoresceinated by using the Mirus fluoresceination reagent (Panvera Inc, see example 1) and then applied on neutravidin microplates. Addition of antifluorescein-AP antibody generated a strong chemiluminescence signal (FIG. 12) in the sample treated with MutY enzyme (i.e. aldehydes were generated), but not in the sample not-treated with MutY (aldehydes not generated).

EXAMPLE 5

Labeling of Mismatches with FARP, BARP or AED: Inactivation of Enzymatic Action during Labeling A DNA sample containing mismatches is dissolved in a buffered solution and treated with a repair glycosylase, either MutY or TDG (1 unit enzyme per µg DNA). The reaction is incubated at 37° C. for 1 hour. Upon completion of the reaction with MutY or TDG, the solution is cooled to 15° C., to arrest enzymatic activity. FARP is added to the sample and allowed to react for 30 minutes at 15° C. At the end of the 30 minute incubation with FARP, the reaction solution is suddenly heated to 70° C. for two minutes to inactivate the enzyme. The sample of DNA is now ready for purification and detection as previously described. Alternatively, instead of heating to 70° C. the enzyme can be solubilized and removed via a standard phenol-chloroform extraction, or via addition of Proteinase K (0.1 mg/ml, 2 h, 37° C.).

EXAMPLE 6

Strategy to Utilize DNA Chips for Detection of Both Inherited Polymorphisms and Mutations, As Well As Acquired Mutations from Cancer Samples The ability to derive both inherited and acquired genetic alterations in a single step over 6800 genes with the present procedure, using the Affymetrix array as an example, is described below.

Inherited single nucleotide polymorphisms (SNPs) are estimated to be present in the two alleles of each gene with a frequency of ~1:1000 bases. When an SNP in the coding sequence causes a debilitating change in the protein, heterozygous mutations arise which could result to early onset of cancer (e.g. the Li-Fraumeni syndrome). When cDNA from normal cells is melted and self-hybridized, mismatches will occur at positions of heterozygocities and SNPs, whenever both alleles are expressed, which will be detectable by the present technology (A.L.B.U.M.S) and would display positive on the DNA arrays. Because SNPs among alleles occur at a high frequency (~1:1000 bp) it is possible that within every single gene (average ~2,000 bp) there is one or more SNPs. Therefore, if both paternal and maternal alleles are transcribed, self-hybridizing cDNA from whole genes would be expected to result in one or more mismatches per gene, as a result of allelic cross-hybridization. All array elements would then display positive, resulting to trivial information. By digesting the cDNA to ~100–200 bp pieces prior to ALBUMS genotypic selection (as described in example 3) the problem is avoided: Most fragments are likely to contain none, or occasionally one inherited SNP. ALBUMS will select mismatch-containing fragments, and array elements that score positive will be only those capturing a 100–200-mer gene fragment with an SNP.

Acquired mutations can be detected by following the same strategy, and by using cancer samples from the same individual as the normal sample. Again, by self-hybridizing cDNA from cancer samples and fragmenting to 100–200-mers, it is likely that most fragments will contain none, or occasionally one inherited SNP, or very occasionally one acquired mutation. Array elements that score positive will be those corresponding to genes that contain either inherited or acquired mutations, but rarely both.

Figure 12:
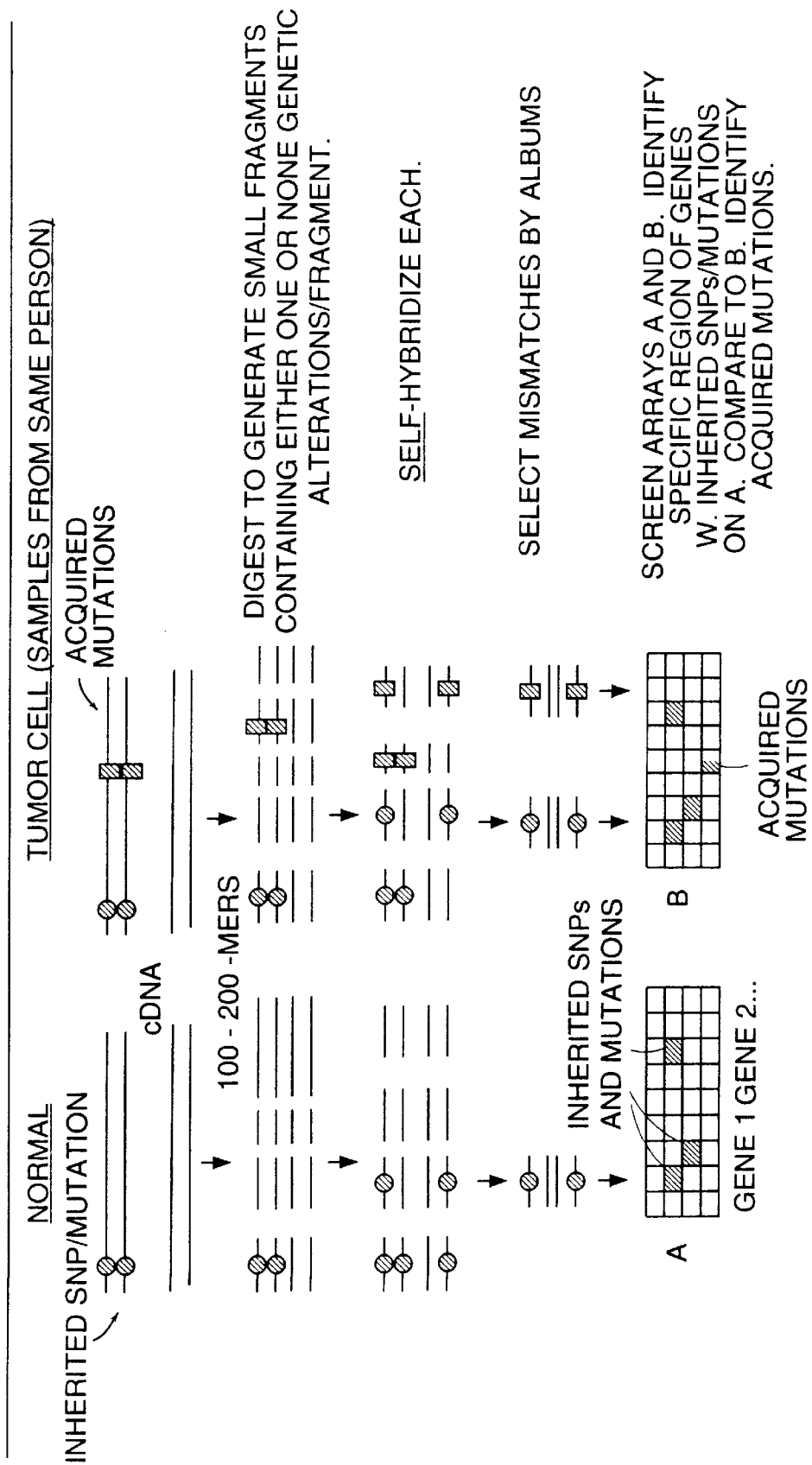
FIG. 12 is a schematic showing how the method of mismatch identification can be used with a DNA chip to detect inherited and acquired predisposition to cancer (see text).

An example of using the high resolution Affymetrix array (described earlier) to detect genetic alterations in parallel normal and cancer samples is displayed in FIG. 12. cDNA from normal tissue is melted and self-hybridized to generate mismatches (FIG. 12), then digested with appropriate enzymes to generate 100–200-mers and add primers; then the present technology, (ALBUMS), utilizing one of the probes (FARP, AED or BARP) selects the mismatches, PCR amplifies them and these are applied on the Affymetrix array: The mutation-containing 200-mers isolated via ALBUMS will cause certain 25-mer array elements to display positive, thereby identifying both the gene and the approximate (+100–200 bp) location of an inherited polymorphism among the two alleles.

Next, cDNA from the cancer sample is melted, self-hybridized and processed similarly. Acquired mutations will show up as positive array elements that are negative on the normal tissue array. Acquired mutations scored on the same gene as an inherited mutation provide candidate genes to be examined for loss of heterozygocity, using existing methodologies. Finally, cDNA from cancerous cells will be cross-hybridized to cDNA from normal cells and the procedure will be repeated (not illustrated in FIG. 12). This will detect acquired mutations in those genes that express a single allele in their mRNA, which would not be detected by self-hybridization alone.

The use of the Clontech array will provide similar information to the Affymetrix array. However, this array would be used with fewer genes and with smaller 'resolution', since the array elements contain 500 bases-long cDNA and it is possible that certain elements will capture both inherited SNPs and acquired mutations, thereby providing unclear information. On the other hand these arrays are simpler to use and do not require the fluorescent laser scanner, hence they are currently more accessible to users.

What is claimed is:

1. A method of identifying a plurality of mutations in a target DNA sequence comprising:
   (a) hybridizing the target DNA sequence with a control DNA sequence wherein said control DNA sequence is the wild-type DNA sequence corresponding to the target DNA sequence to create a duplex;
   (b) treating the duplex to remove any spontaneous aldehydes;
   (c) reacting the duplex with a repair glycosylase to convert any mismatched sites in the duplex to reactive sites containing an aldehyde-containing abasic site;
   (d) reacting the duplex with a compound of the formula X-Z-Y, wherein X is a detectable moiety, Y is NHNH$_2$, O—NH$_2$ or NH$_2$, and Z is a hydrocarbon, alkyhydroxy, alkylethoxy, alkylester, alkylether, alkylamide or alkylamine, wherein Z may be substituted or unsubstituted; and wherein Z may contain a cleavable group; for a sufficient time and under conditions to covalently bind to the reactive sites;
   (e) detecting the bound compound to identify sites of mismatches;
   (f) determining where each mismatch occurs; and
   (g) determining whether each mismatch is a mutation or polymorphisms.

2. The method of claim 1, where the detectable moiety is selected from the group consisting of NH$_2$, SH, NHNH$_2$, a fluorescein derivative, a hydroxycoumarin derivative, a rhodamine derivative, a BODIPY derivative, a digoxigenin derivative and a biotin derivative.

3. The method of claim 1, wherein the compound has the formula:

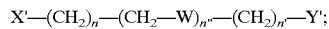

wherein

X' is NHNH$_2$ or NH$_2$;

Y' is O—NH$_2$ or NH$_2$;

W is —NHC(O)—, —NHC(OH)—, —C(OH)—, —NH—, C—O—, —O—, —S—, —S—S, —OC(O)—, or C(O)O—;

n is an integer from 0 to 12;

n' is an integer from 0 to 12, and n" is an integer from 1 to 4.

4. The method of claim 3, wherein the compound has a molecular weight between 100–500.

5. The method of claim 4, wherein the compound has a molecular weight between 150–200.

6. The method of claim 3, wherein the compound has the formula:

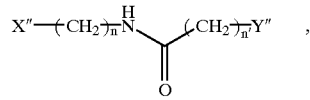

wherein X', Y', n, and n' are as defined as above.

7. The method of claim 6, wherein the compound has the formula

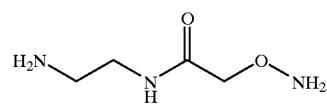

(2-(aminoacetylamino) ethylenediamine).

8. The method of claim 1, wherein the compound has the formula;

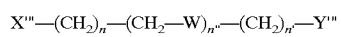

wherein

Y''' is O—NH$_2$;

X''' is a fluorescent molecule, a fluorescein derivative or a hydroxy-coumarin derivative;

W is —NHC(O)—, —NHC(OH)—, —C(OH)—, —NH—, C—O—, —O—, —S—, —OC(O)—, or C(O)O—;

n is an integer from 0 to 12;

n' is an integer from 0 to 12, and n" is an integer from 1 to 4.

9. The method of claim 8, wherein the compound is

[structure: fluorescein-based compound with linker ending in O-NH2]

or

[structure: hydroxycoumarin-based compound with linker ending in O-NH2]

10. The method of claim 1, wherein the compound has the formula $$X''''-(CH_2)_n-(CH_2-W)_{n''}-(CH_2)_{n'}-Y''';$$

wherein

Y''' is O—NH$_2$ or NHNH$_2$;

X'''' is a detectable molecule, biotin or biotin derivative.

W is —NHC(O)—, —NHC(OH)—, —C(OH)—, —NH—, C—O—, —O—, —S—, —S—S, —OC(O)—, or C(O)O—;

n is an integer from 0 to 12;

n' is an integer from 0 to 12, and n'' is an integer from 1 to 4.

11. The method of claim 10, wherein the compound is

[structure: biotin-hydrazide-aminooxy compound]

or

[structure: biotin-hydrazide compound]

12. The method of claim 1 where in the mismatch repair glycosylase is MutY or TDG.

13. A method of identifying a plurality mutations in a target DNA sequence comprising:

(a) hybridizing the target DNA sequence with a control DNA sequence wherein said control DNA sequence is the wild-type DNA sequence corresponding to the target DNA sequence to create a duplex;

(b) digesting the duplex to fragments of 50–300 base pairs, with restriction enzymes that allow generic addition of PCR primers;

(c) adding PCR primers to the duplex (d) treating the duplex to remove any spontaneous aldehydes;

(e) reacting the duplex with a repair glycosylase to convert any mismatched sites in the duplex to reactive sites containing an aldehyde-containing abasic site;

(f) reacting the duplex with a compound of the formula X-Z-Y, where X is a detectable moiety, Y is NHNH$_2$, O—NH$_2$ or NH$_2$ and Z is a hydrocarbon, alkyhydroxy, alkylethoxy, alkylester, alkylether, alkylamide or alkylamine, wherein Z may be substituted or unsubstituted; and where Z may contain a cleavable group; for a sufficient time and under conditions to covalently bind to the reactive sites;

(g) isolating the DNA that contains mismatches from DNA without mismatches;

(h) PCR-amplifying the mismatch-containing DNA;

(i) detecting the DNA that contains mismatches, as well as the genomic position of the mismatch; and (j) determining whether the mismatch is a mutation or polymorphism.

14. The method of claim 13, where the mismatch repair glycosylase is MutY or TDG.

15. The method of claim 13, where the detectable moiety is selected from the group consisting of NH$_2$, SH, NHNH$_2$, a fluorescein derivative, a hydroxycoumarin derivative, a rhodamine derivative, a BODIPY derivative, a digoxigenin derivative and a biotin derivative.

16. The method of claim 13, wherein the compound has the formula:

$$X'-(CH_2)_n-(CH_2-W)_{n''}-(CH_2)_{n'}-Y';$$

wherein

X' is NHNH$_2$ or NH$_2$;

Y' is O—NH$_2$ or NH$_2$;

W is —NHC(O)—, —NHC(OH)—, —C(OH)—, —NH—, C—O—, —O—, —S—, —S—S, —OC(O)—, or C(O)O—;

n is an integer from 0 to 12;

n' is an integer from 0 to 12, and n'' is an integer from 1 to 4.

17. The method of claim 16, wherein the compound has a molecular weight between 100–500.

18. The method of claim 17, wherein the compound has a molecular weight between 150–200.

19. The method of claim 16, wherein the compound has the formula:

$$X''-(CH_2)_n-\underset{\underset{O}{\|}}{N}(H)-C-(CH_2)_{n'}-Y'' ,$$

wherein X', Y', n, and n' are as defined as above.

20. The method of claim 19, wherein the compound has the formula

[Structure: H2N-CH2CH2-NH-C(=O)-CH2-O-NH2]

(2-(aminoacetylamino) ethylenediamine).

21. The method of claim 13, wherein the compound has the formula;

$$X'''-(CH_2)_n-(CH_2-W)_{n''}-(CH_2)_{n'}-Y'''$$

wherein

Y''' is O—NH$_2$;

X''' is a fluorescent molecule, a fluorescein derivative or a hydroxy-coumarin derivative;

W is —NHC(O)—, —NHC(OH)—, —C(OH)—, —NH—, C—O—, —O—, —S—, —OC(O)—, or C(O)O—;

n is an integer from 0 to 12;

n' is an integer from 0 to 12, and n" is an integer from 1 to 4.

22. The method of claim 21, wherein the compound is

[Structure: fluorescein derivative connected via HN-C(=O)-CH2-S-CH2-C(=O)-NH-NH-C(=O)-CH2-O-NH2]

or

[Structure: 7-hydroxycoumarin derivative connected via C(=O)-NH-(CH2)n-NH-C(=O)-NH-C(=O)-CH2-O-NH2]

23. The method of claim 22, wherein the compound has the formula $$X''''-(CH_2)_n-(CH_2-W)_{n''}-(CH_2)_{n'}-Y''''$$;

wherein

Y'''' is O—NH$_2$ or NHNH$_2$;

X'''' is a detectable molecule, biotin or biotin derivative.

W is —NHC(O)—, —NHC(OH)—, —C(OH)—, —NH—, C—O—, —O—, —S—, —S—S, —OC(O)—, or C(O)O—;

n is an integer from 0 to 12;

n' is an integer from 0 to 12, and n" is an integer from 1 to 4.

24. The method of claim 23, wherein the compound is

[Structure: biotin connected to -C(=O)-NH-NH-C(=O)-CH2-O-NH2]

or

[Structure: biotin connected to -C(=O)-NH-NH2]

25. The method of claim 1, wherein the target DNA sequence contains a plurality of genes.

26. The method of claim 13, wherein the target DNA contains a plurality of genes.

27. The method of claim 25, wherein the nucleotide sequence of the target DNA is not known.

28. The method of claim 26, wherein the nucleotide sequence of the target DNA is not known.

29. A method of using aldehyde-containing abasic sites in a target DNA sequence to identify a plurality of changes from a wild type DNA sequence comprising:

(a) hybridizing the target DNA sequence with a control DNA sequence wherein said control DNA sequence is the wild type DNA sequence corresponding to the target DNA sequence to create a duplex;

(b) treating the duplex to remove any spontaneous aldehydes;

(c) reacting the duplex with a repair glycosylase to convert any mismatched sites in the duplex to reactive sites containing an aldehyde containing abasic site;

(d) reacting the duplex with a compound of the formula X-Z-Y, wherein X is a detectable moiety, Y is NHNH$_2$, O—NH$_2$ or NH$_2$, and Z is a hydrocarbon, alkyhydroxy, alkylethoxy, alkylester, alkylether, alkylamide or alkylamine, wherein Z may be substituted or unsubstituted; and wherein Z may contain a cleavable group; for a sufficient time and under conditions to covalently bind to the reactive sites;

(e) detecting the bound compound to identify the abasic sites; and (f) determining where each abasic site occurs to identify said plurality of changes from said wild type DNA sequence in said target DNA sequence.

30. The method of claim 29 wherein the repair glycosylase is MutY or TDG.

* * * * *

UNITED STATES PATENT AND TRADEMARK OFFICE
CERTIFICATE OF CORRECTION

PATENT NO. : 6,174,680 B1 Page 1 of 1
DATED : January 16, 2001
INVENTOR(S) : Gerassimos M. Makrigiorgos It is certified that error appears in the above-identified patent and that said Letters Patent is hereby corrected as shown below:

Column 31,
Line 60, delete "alkyhydroxy" and insert therefor -- alkylhydroxy --.

Column 32,
Line 3, delete "polymorphisms" and insert therefor -- a polymorphism --.
Line 51, delete ";".
Line 39, between "wherein" and " X' ", insert -- X" is --.
Line 39, between " X' ", and " Y' " insert -- Y" is --.

Column 33,
Line 28, delete "." and insert therefor -- ; --.
Line 59, between "plurality" and "mutations", insert -- of --.

Column 34,
Line 1, after "duplex" insert -- ; --.
Line 10, delete "alkyhydroxy" and insert therefor -- alkylhydroxy --.
Line 67, between "wherein" and " X' ", insert -- X" is --.
Line 67, between " X' ", and " Y' " insert -- Y" is --.

Column 35,
Line 11, delete ";".
Line 55, delete "." and replace therefor -- ; --.

Column 36,
Line 46, delete "alkyhydroxy" and insert therefor -- alkylhydroxy --.

Signed and Sealed this

Thirteenth Day of August, 2002

*Attest:*

JAMES E. ROGAN
*Attesting Officer*   *Director of the United States Patent and Trademark Office*